(12) United States Patent
Venturino et al.

(10) Patent No.: US 7,568,900 B2
(45) Date of Patent: *Aug. 4, 2009

(54) APPARATUS FOR MAKING A REINFORCED FIBROUS ABSORBENT MEMBER

(75) Inventors: Michael B. Venturino, Appleton, WI (US); Susan J. Daniels, Neenah, WI (US); David W. Heyn, Neenah, WI (US); James M. Kaun, Neenah, WI (US); Derek P. Murphy, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/677,857

(22) Filed: Feb. 22, 2007

(65) Prior Publication Data

US 2007/0248708 A1 Oct. 25, 2007

Related U.S. Application Data

(60) Continuation of application No. 10/917,115, filed on Aug. 12, 2004, now Pat. No. 7,204,682, which is a division of application No. 10/306,269, filed on Nov. 27, 2002, now Pat. No. 6,989,118.

(60) Provisional application No. 60/350,079, filed on Jan. 15, 2002.

(51) Int. Cl.
    *B27N 3/04* (2006.01)
(52) U.S. Cl. ..................... 425/81.1; 425/83.1
(58) Field of Classification Search .......... 425/81.1, 425/83.1
    See application file for complete search history.

(56) References Cited

U.S. PATENT DOCUMENTS 2,161,539 A 6/1939 Swartz
2,964,039 A 12/1960 Johnson, Jr. et al.

(Continued)

FOREIGN PATENT DOCUMENTS

AU 458424 2/1975

(Continued)

OTHER PUBLICATIONS

International Search Report for PCT/US03/15959 dated Feb. 3, 2004.

(Continued)

*Primary Examiner*—Robert B Davis
*Assistant Examiner*—Joseph Leyson
(74) *Attorney, Agent, or Firm*—Armstrong Teasdale, LLP

(57) ABSTRACT

Apparatus for making a reinforced absorbent member includes a forming chamber adapted to contain a fluent fibrous material. A forming surface is moveable within the forming chamber along an arcuate path generally from an entrance of the forming chamber to an exit thereof. The forming surface is adapted to collect fibrous material thereon to form the absorbent member. A source of reinforcing web is disposed generally exterior of the forming chamber. The forming chamber has an opening through which the reinforcing web is received into the forming chamber for subsequent conveyance within the forming chamber toward the forming surface. The opening is disposed downstream of the forming chamber entrance generally in the direction of movement of the forming surface along the path.

8 Claims, 12 Drawing Sheets

U.S. PATENT DOCUMENTS

| | | | |
|---|---|---|---|
| 3,085,309 A | 4/1963 | Olson | |
| 3,156,751 A | 11/1964 | Valdes et al. | |
| 3,587,579 A | 6/1971 | Sabee | |
| 3,629,047 A | 12/1971 | Davison | |
| 3,683,921 A | 8/1972 | Brooks et al. | |
| 3,768,479 A | 10/1973 | Widlund | |
| 3,816,231 A | 6/1974 | Marshall | |
| 3,856,012 A | 12/1974 | MacDonald et al. | |
| 3,862,877 A | 1/1975 | Camden | |
| 3,867,935 A | 2/1975 | Eisdorfer et al. | |
| 3,888,248 A | 6/1975 | Moore et al. | |
| 3,935,979 A | 2/1976 | Hickey | |
| 4,001,472 A | 1/1977 | Thomas et al. | |
| 4,028,455 A | 6/1977 | Ueda et al. | |
| 4,141,772 A | 2/1979 | Buell | |
| 4,217,078 A | 8/1980 | Buell | |
| 4,235,237 A | 11/1980 | Mesek et al. | |
| 4,300,562 A | 11/1981 | Pieniak | |
| 4,303,189 A | 12/1981 | Wiley et al. | |
| 4,392,862 A | 7/1983 | Marsan et al. | |
| 4,425,127 A | 1/1984 | Suzuki et al. | |
| 4,606,964 A | 8/1986 | Wideman | |
| 4,639,253 A | 1/1987 | Dyer et al. | |
| 4,640,810 A | 2/1987 | Laursen et al. | |
| 4,645,499 A | 2/1987 | Rupinskas | |
| 4,666,647 A | 5/1987 | Enloe et al. | |
| 4,674,966 A | 6/1987 | Johnson et al. | |
| 4,704,112 A | 11/1987 | Suzuki et al. | |
| 4,710,185 A | 12/1987 | Sneyd, Jr. et al. | |
| 4,761,258 A | 8/1988 | Enloe | |
| 4,764,325 A | 8/1988 | Angstadt | |
| 4,765,780 A | 8/1988 | Angstadt | |
| 4,773,903 A | 9/1988 | Weisman et al. | |
| 4,775,579 A | 10/1988 | Hagy et al. | |
| 4,810,568 A | 3/1989 | Buyofsky et al. | |
| 4,834,735 A | 5/1989 | Alemany et al. | |
| 4,837,715 A | 6/1989 | Ungpiyakul et al. | |
| 4,904,440 A | 2/1990 | Angstadt | |
| 4,908,175 A | 3/1990 | Angstadt | |
| 4,915,897 A | 4/1990 | Farrington et al. | |
| 4,915,993 A | 4/1990 | Ten Wolde | |
| 4,927,346 A | 5/1990 | Kaiser et al. | |
| 4,927,582 A | 5/1990 | Bryson | |
| 5,004,579 A | 4/1991 | Wislinski et al. | |
| 5,017,324 A | 5/1991 | Kaiser et al. | |
| 5,124,188 A | 6/1992 | Roe et al. | |
| 5,128,082 A | 7/1992 | Makoui | |
| 5,139,841 A | 8/1992 | Makoui et al. | |
| 5,144,729 A | 9/1992 | Austin et al. | |
| 5,161,283 A | 11/1992 | Hansen | |
| 5,219,633 A | 6/1993 | Sabee | |
| 5,281,208 A | 1/1994 | Thompson et al. | |
| 5,302,445 A | 4/1994 | DePetris et al. | |
| 5,328,072 A | 7/1994 | Ruessmann et al. | |
| 5,334,446 A | 8/1994 | Quantrille et al. | |
| 5,389,095 A | 2/1995 | Suzuki et al. | |
| 5,389,202 A | 2/1995 | Everhart et al. | |
| 5,429,788 A | 7/1995 | Ribble et al. | |
| 5,447,677 A | 9/1995 | Griffoul et al. | |
| 5,466,409 A | 11/1995 | Partridge et al. | |
| 5,486,167 A | 1/1996 | Dragoo et al. | |
| 5,505,720 A | 4/1996 | Walters et al. | |
| 5,514,120 A | 5/1996 | Johnston et al. | |
| 5,527,300 A | 6/1996 | Sauer | |
| 5,531,729 A | 7/1996 | Coles et al. | |
| 5,591,148 A | 1/1997 | McFall et al. | |
| 5,607,415 A | 3/1997 | Datta et al. | |
| 5,614,283 A | 3/1997 | Potnis et al. | |
| 5,662,581 A | 9/1997 | Jennrich et al. | |
| 5,672,306 A | 9/1997 | Sprang et al. | |
| 5,704,931 A | 1/1998 | Holtman et al. | |
| 5,756,039 A | 5/1998 | McFall et al. | |
| 5,762,844 A | 6/1998 | Van Himbergen et al. | |
| 5,772,813 A | 6/1998 | Bitowft et al. | |
| 5,803,334 A | 9/1998 | Patel et al. | |
| 5,818,719 A | 10/1998 | Brandon et al. | |
| 5,866,173 A | 2/1999 | Reiter et al. | |
| 5,871,613 A | 2/1999 | Bost et al. | |
| 5,873,963 A | 2/1999 | Trombetta et al. | |
| 5,902,757 A | 5/1999 | Stern et al. | |
| 5,916,661 A | 6/1999 | Benson et al. | |
| 5,925,439 A | 7/1999 | Haubach | |
| 5,938,648 A | 8/1999 | LaVon et al. | |
| 5,944,706 A | 8/1999 | Palumbo et al. | |
| 5,947,945 A | 9/1999 | Cree et al. | |
| 5,961,509 A | 10/1999 | Kling | |
| 5,997,520 A | 12/1999 | Ahr et al. | |
| 6,048,489 A | 4/2000 | Reiter et al. | |
| 6,060,637 A | 5/2000 | Bitowft et al. | |
| 6,090,994 A | 7/2000 | Chen | |
| 6,107,538 A | 8/2000 | Young et al. | |
| 6,203,654 B1 | 3/2001 | McFall et al. | |
| 6,204,207 B1 | 3/2001 | Cederblad et al. | |
| 6,220,999 B1 | 4/2001 | Kugler et al. | |
| 6,258,996 B1 | 7/2001 | Goldman | |
| 6,262,331 B1 | 7/2001 | Nakahata et al. | |
| 6,284,943 B1 | 9/2001 | Osborn, III et al. | |
| 6,296,862 B1 | 10/2001 | Paul et al. | |
| 6,330,735 B1 | 12/2001 | Hahn et al. | |
| 6,375,644 B2 | 4/2002 | Mizutani | |
| 6,416,697 B1 | 7/2002 | Venturino et al. | |
| 6,492,574 B1 | 12/2002 | Chen et al. | |
| 6,533,978 B1 | 3/2003 | Wisneski et al. | |
| 6,533,989 B1 | 3/2003 | Wisneski et al. | |
| 6,575,948 B1 | 6/2003 | Kashiwagi et al. | |
| 6,630,096 B2 | 10/2003 | Venturino et al. | |
| 7,094,373 B2 * | 8/2006 | Heyn et al. | 264/101 |
| 7,204,682 B2 * | 4/2007 | Venturino et al. | 425/82.1 |
| 2001/0027305 A1 | 10/2001 | Raidel et al. | |
| 2001/0039405 A1 | 11/2001 | Kuehn, Jr. et al. | |
| 2003/0116888 A1 | 6/2003 | Rymer et al. | |
| 2003/0119401 A1 | 6/2003 | Chakravarty et al. | |
| 2003/0132556 A1 | 7/2003 | Venturino et al. | |
| 2003/0139721 A1 | 7/2003 | Melius et al. | |
| 2004/0092898 A1 | 5/2004 | Schäfer et al. | |
| 2004/0102752 A1 | 5/2004 | Chen et al. | |

FOREIGN PATENT DOCUMENTS

| | | |
|---|---|---|
| DE | 198 23 954 | 12/1999 |
| EP | 0 151 018 A2 | 8/1985 |
| EP | 0 226 939 | 7/1987 |
| EP | 0 297 180 | 1/1989 |
| EP | 0 298 348 | 1/1989 |
| EP | 0 399 511 | 11/1990 |
| EP | 0 467 409 A1 | 1/1992 |
| GB | 2168612 A | 6/1986 |
| JP | 09-122172 A | 5/1997 |
| JP | 10-211236 A | 8/1998 |
| WO | WO 93/18729 A1 | 9/1993 |
| WO | WO 96/00550 A1 | 1/1996 |
| WO | WO 97/05840 | 2/1997 |
| WO | WO 98/22064 A1 | 5/1999 |
| WO | WO 99/22685 A1 | 5/1999 |
| WO | WO 99/25281 A1 | 5/1999 |
| WO | WO 00/10498 A1 | 3/2000 |
| WO | WO 00/37000 A1 | 6/2000 |
| WO | WO 00/37725 A1 | 6/2000 |
| WO | WO 00/56257 A1 | 9/2000 |
| WO | WO 00/63479 A1 | 10/2000 |
| WO | WO 01/92003 A1 | 12/2001 |

WO    WO 03/059232 A2    7/2003

OTHER PUBLICATIONS

International Search Report for PCT/US03/16480 dated Oct. 13, 2003.

International Search Report for PCT/US04/008428 dated Aug. 23, 2004.

International Search Report for PCT/US04/006915 dated Nov. 5, 2004.

* cited by examiner

APPARATUS FOR MAKING A REINFORCED FIBROUS ABSORBENT MEMBER

REFERENCE TO RELATED APPLICATIONS

This continuation patent application claims priority from U.S. patent application Ser. No. 10/917,115 filed on Aug. 12, 2004 (now U.S. Pat. No. 7,204,682), which is a divisional of U.S. patent application Ser. No. 10/306,269 filed on Nov. 27, 2002 (now U.S. Pat. No. 6,989,118). U.S. patent application Ser. No. 10/306,269 claims priority from provisional application Ser. No. 60/350,079 filed on Jan. 15, 2002 and entitled "Scrim Reinforced Absorbent." Each of these applications are hereby incorporated by reference in their entireties.

BACKGROUND OF THE INVENTION

This invention relates generally to a process and apparatus for making absorbent members such as an absorbent core used for articles such as disposable diapers, children's training pants, feminine care articles, incontinence articles and the like, and more particularly to such an absorbent member which is constructed of a fibrous material and has a reinforcing web incorporated therein.

One common method of forming fibrous absorbent members employs conventional air forming techniques in which a fibrous sheet of cellulosic or other suitable absorbent material is fiberized in a conventional fiberizer or other shredding or comminuting device to form a fluidized flow of discrete fibers. Particles of superabsorbent material may also be mixed with the discrete fibers. The mixture of fibers and superabsorbent particles are entrained in an air stream within a forming chamber and directed by the air stream to a foraminous forming surface that moves within the forming chamber. The air passes through the forming surface while the fibers and superabsorbent particles are collected on the forming surface to form a fibrous absorbent member. In addition, bonding agents or other strengthening components may be incorporated to provide a stabilized absorbent member. The absorbent member may then be stored or immediately directed for further processing and assembly with other components to produce an absorbent article.

Other conventional techniques, such as dry-forming techniques, wet-laying techniques, foam-forming techniques, and various wet-forming techniques, have also been employed to form stabilized absorbent members. The resulting absorbent members have included absorbent fibers, natural fibers, synthetic fibers, superabsorbent materials, binders, and strengthening components in desired combinations.

Absorbent members may also be strengthened by adding reinforcing materials, such as reinforcement filaments, tissue layers, fabric layers and netting materials to the fibrous material. For example, co-assigned U.S. patent application Ser. No. 10/306,086 entitled "Absorbent Article with Reinforced Absorbent Structure," filed Nov. 27, 2002 by David W. Heyn et al. (attorney docket no. K-C 16,836), the entire disclosure of which is incorporated herein by reference, discloses a reinforced fibrous absorbent member comprised of a fibrous material and a scrim (e.g., netting or mesh material) incorporated within the fibrous material to strengthen the absorbent member and reduce the risk of cracking thereof during use.

European Patent Application EP 0467409 A1 also discloses an absorbent pad having a reinforcing web therein. The reinforcing web comprises longitudinally and laterally intersecting strands. Some or all of the strands are formed of an inner first polymeric material having a first melting point and an outer second polymeric material having a second melting point lower than the first melting point. The reinforcing web is introduced into a forming chamber containing fluidized fibrous material which is deposited on a drum. The openings defined by the intersecting strands of the web are sized sufficiently large to permit the fibrous material to pass through the web to a forming surface to form a first layer of the pad. The web is then laid on the first pad layer and a second layer is formed over the web. The entire pad is then heated to melt the second, but not the first, polymeric material of the web strands to fuse the web between the first and second layers of the absorbent pad.

However, a suitable process and apparatus for forming a reinforced fibrous absorbent member without the need for bonding or otherwise adhesively securing a reinforcing web within the absorbent member has heretofore been unknown. In particular, there is a need for a process and apparatus which delivers a continuous web of scrim into an air forming apparatus in a manner that facilitates proper alignment and securement of the scrim within the fibrous absorbent member to inhibit separation of the fibrous material from the scrim.

SUMMARY OF THE INVENTION

In one aspect, apparatus for making a reinforced absorbent member including a fibrous material and a porous reinforcing web having inner and outer surfaces generally comprises a forming chamber adapted to contain a fluent fibrous material. A forming surface is moveable within the forming chamber along an arcuate path generally from an entrance of the forming chamber to an exit thereof. The forming surface is adapted to collect fibrous material thereon to form the absorbent member. A source of reinforcing web is disposed generally exterior of the forming chamber. The forming chamber has an opening through which the reinforcing web is received into the forming chamber for subsequent conveyance within the forming chamber toward the forming surface. The opening is disposed downstream of the forming chamber entrance generally in the direction of movement of the forming surface along the path.

In another aspect, apparatus for making a reinforced absorbent member including a fibrous material and a reinforcing web having inner and outer surfaces generally comprises a forming chamber adapted to receive a fluent fibrous material therein. A forming surface is moveable within the forming chamber and adapted to collect fibrous material thereon to form the absorbent member. A source of reinforcing web is disposed generally exteriorly of the forming chamber. A delivery tube has an inlet end open to the exterior of the forming chamber, a discharge end open to the interior of the forming chamber, and a central passage extending between the inlet end and the discharge end. At least a portion of the delivery tube adjacent the discharge end thereof extends within the interior of the forming chamber. The delivery tube is arranged for receiving the reinforcing web from the source of reinforcing web into the central passage of the tube at the inlet end thereof and guiding the web to the discharge end thereof for conveyance within the forming chamber toward the forming surface. The delivery tube forms no part of the forming chamber and is supported by the forming chamber.

In yet another aspect, apparatus for making a reinforced absorbent member including a fibrous material and a reinforcing web having inner and outer surfaces generally comprises a forming chamber adapted to receive a fluent fibrous material therein. A forming surface is moveable within the forming chamber and adapted to collect fibrous material thereon to form the absorbent member. A source of reinforcing web is disposed generally exteriorly of the forming chamber. An elongate delivery tube has an inlet end open to the exterior of the forming chamber, a discharge end open to the interior of the forming chamber adjacent the forming surface, and a central passage extending between the inlet end and the discharge end. At least a portion of the delivery tube adjacent the discharge end thereof extends within the interior of the forming chamber. The delivery tube is arranged for receiving the reinforcing web from the source of reinforcing web into the central passage of the tube at the inlet end thereof and guiding the web to the discharge end thereof for conveyance within the forming chamber toward the forming surface.

In a further aspect, apparatus for making a reinforced absorbent member including a fibrous material and a reinforcing web having inner and outer surfaces comprises a forming chamber adapted to receive a fluent fibrous material therein. A forming surface is moveable within the forming chamber and adapted to collect fibrous material thereon to form the absorbent member. A source of reinforcing web is disposed generally exteriorly of the forming chamber. An elongate delivery tube has an inlet end open to the exterior of the forming chamber, a discharge end open to the interior of the forming chamber, and a central passage extending between the inlet end and the discharge end. At least a portion of the delivery tube adjacent the discharge end thereof extends within the interior of the forming chamber. The delivery tube is arranged for receiving the reinforcing web from the source of reinforcing web into the central passage of the tube at the inlet end thereof and guiding the web to the discharge end thereof for conveyance within the forming chamber toward the forming surface. The delivery tube is disposed at an angle relative to the forming surface.

In still another aspect, apparatus for making a reinforced absorbent member including a fibrous material and a reinforcing web having inner and outer surfaces generally comprises a forming chamber adapted to receive a fluent fibrous material therein. A forming surface is moveable within the forming chamber and adapted to collect fibrous material thereon to form the absorbent member. A source of reinforcing web is disposed generally exteriorly of the forming chamber. An elongate delivery tube has an inlet end open to the exterior of the forming chamber, a discharge end open to the interior of the forming chamber, and a central passage extending between the inlet end and the discharge end. The delivery tube is arranged for receiving the reinforcing web from the source of reinforcing web into the central passage of the tube at the inlet end thereof and guiding the web to the discharge end thereof for conveyance within the forming chamber toward the forming surface. The delivery tube is sized and configured to permit passage of the web therethrough with the web in a generally planar configuration.

BRIEF DESCRIPTION OF THE DRAWINGS

Corresponding reference characters indicate corresponding parts throughout the several views of the drawings.

DETAILED DESCRIPTION OF THE DRAWINGS

Figure 1:
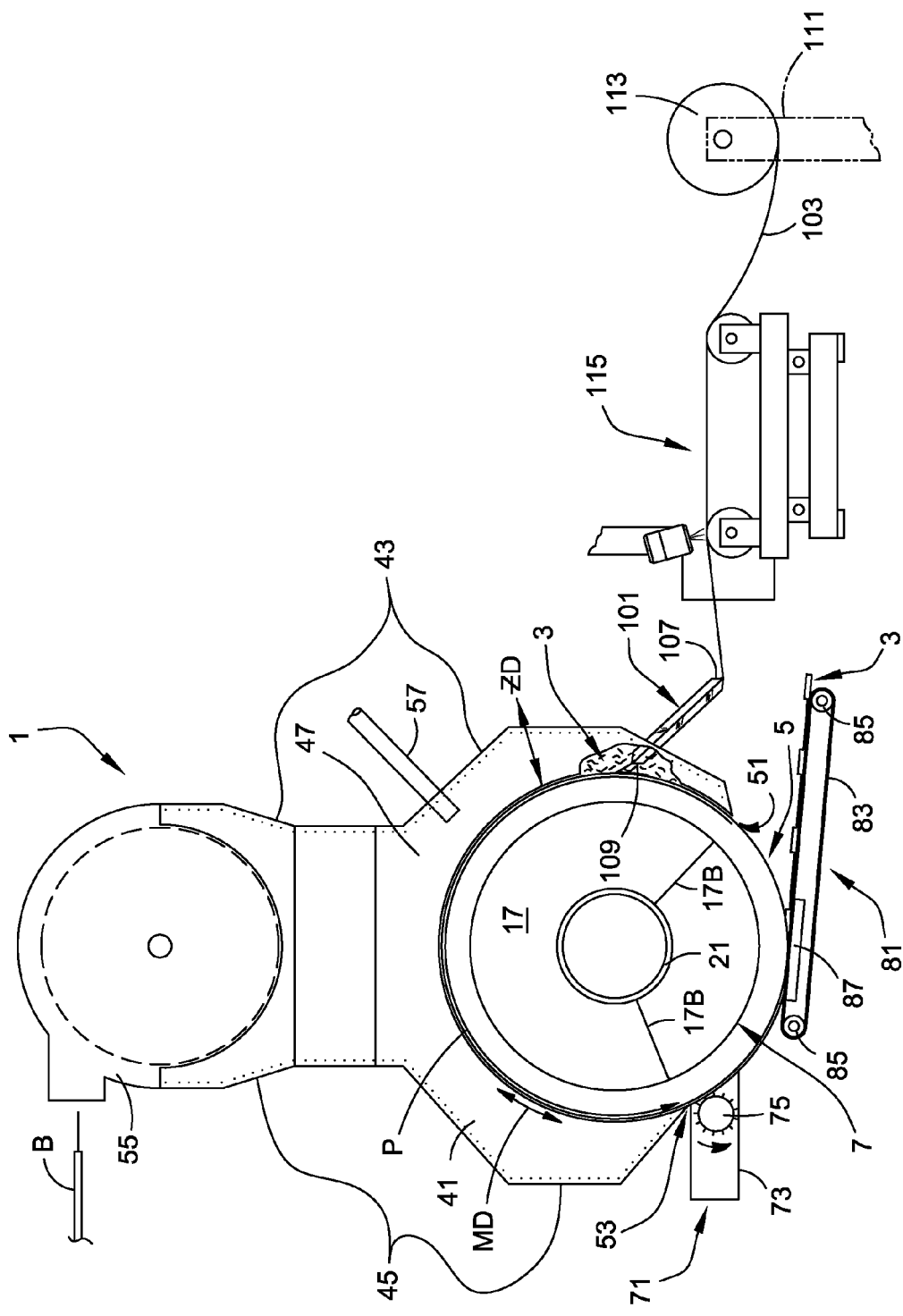
FIG. 1 is a schematic, side elevation of apparatus for forming a reinforced fibrous absorbent member.

The present invention is generally directed to a process and apparatus, indicated generally as 1 in FIG. 1, for making a reinforced fibrous absorbent member, generally indicated at 3, including fibrous material and/or other particulate material and a reinforcing web which strengthens the absorbent member. In particular aspects, the absorbent member 3 can be further used as an absorbent core within disposable personal care products such as diapers, children's training pants, adult incontinence products, feminine care products, medical garments, bandages and the like.

Figure 2:
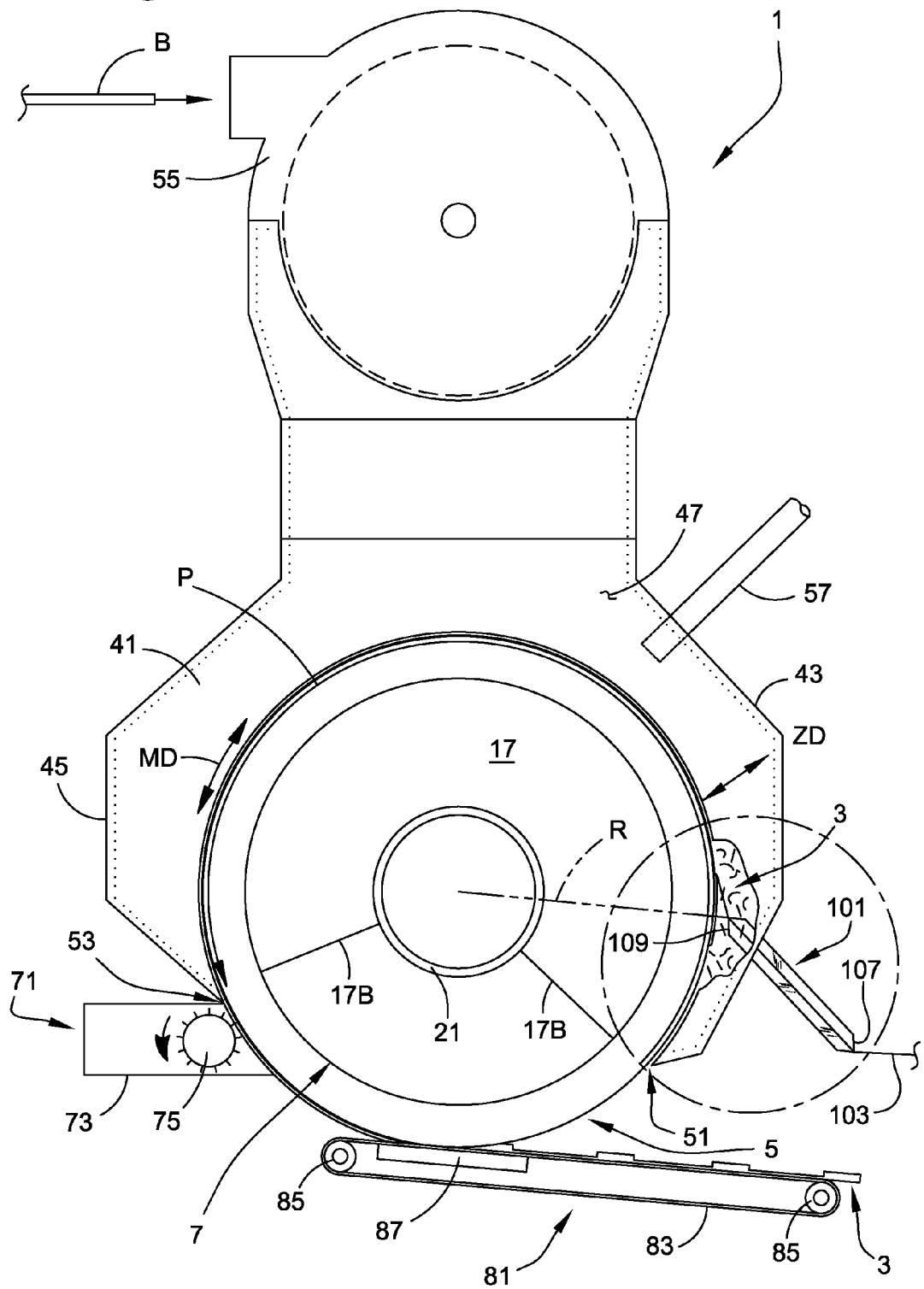
FIG. 2 is an enlarged side elevation of a portion of the apparatus of FIG. 1.
Figure 3:
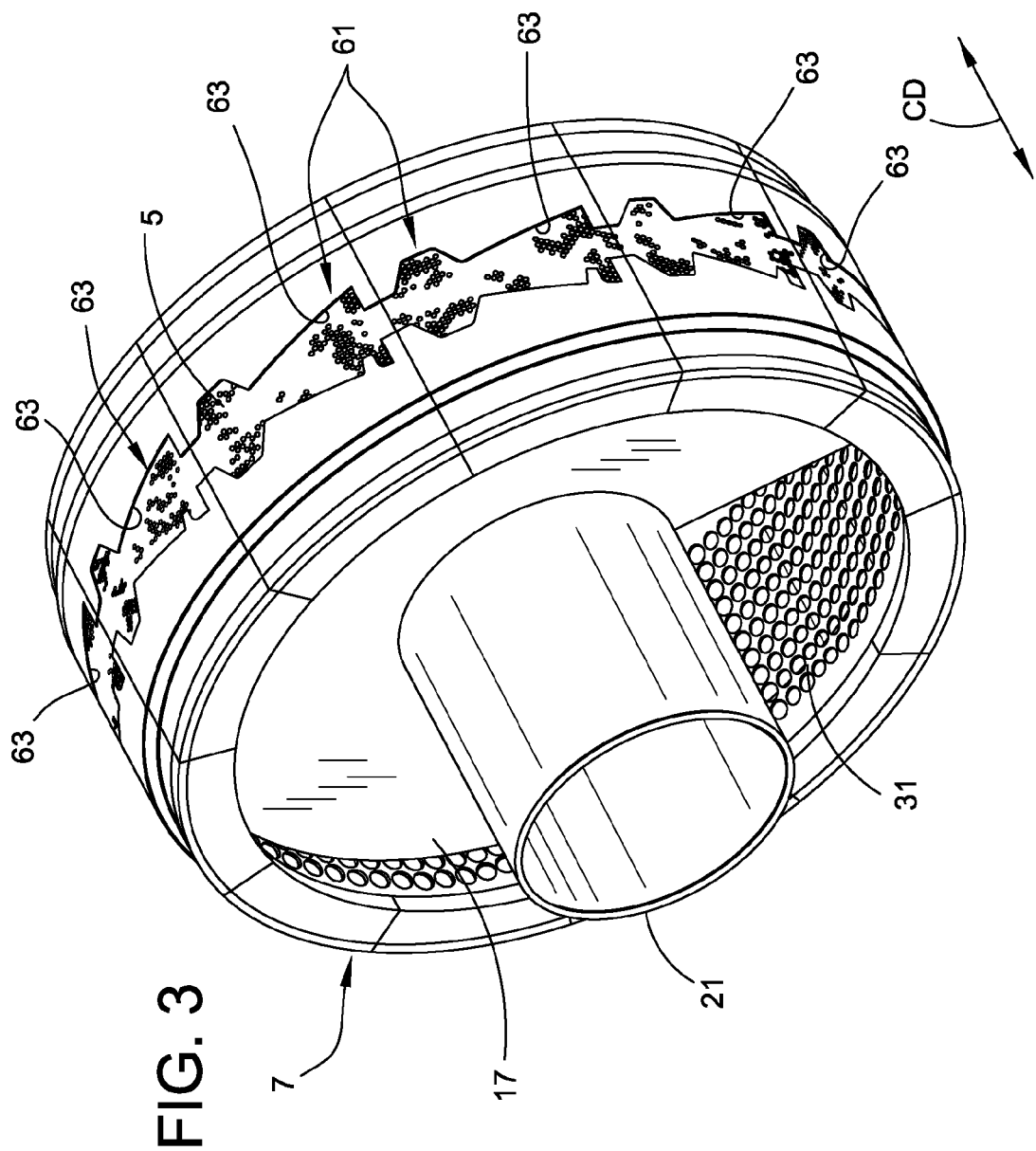
FIG. 3 is a schematic perspective of a forming drum of the apparatus of FIG. 1.

With particular reference to FIGS. 1 and 2, and for the purpose of describing the present invention, the apparatus 1 has an appointed machine-direction MD extending generally in a direction that the absorbent member, or a particular component or material thereof, is transported lengthwise along and through a particular, local position of the apparatus. A cross-machine direction CD (FIGS. 3 and 4) of the apparatus 1 lies generally within the plane of the absorbent member 3, or particular component or material thereof, and is transverse to the machine-direction MD. A Z-direction ZD of the apparatus 1 is substantially perpendicular to both the machine-direction MD and the cross-machine direction CD, and extends generally along a depth-wise, thickness dimension of the absorbent member 3 formed by the apparatus.

Figure 4:
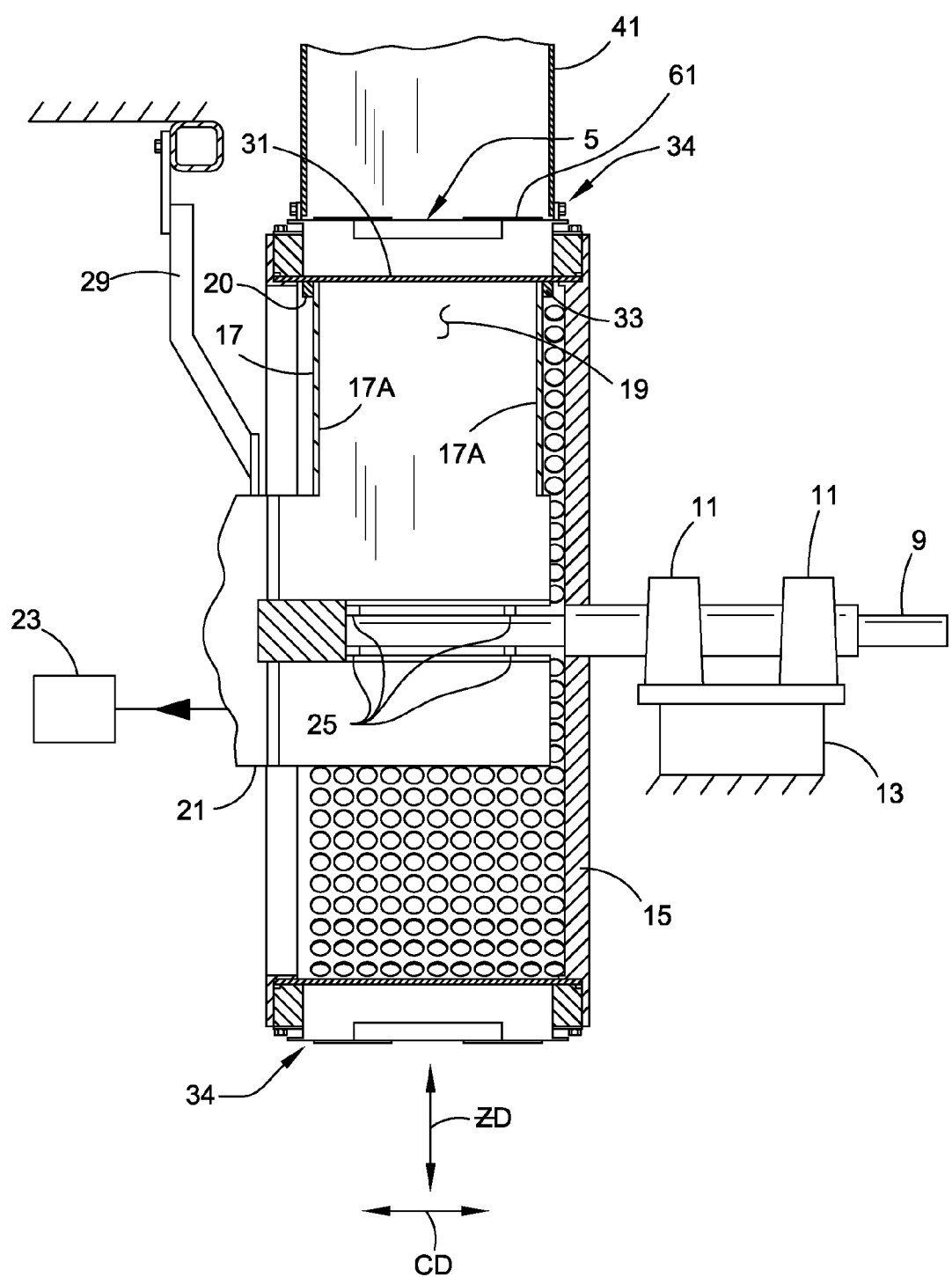
FIG. 4 is a fragmentary cross-section of the apparatus of FIG. 1.

The apparatus 1 comprises a movable, foraminous forming surface 5 extending about the circumference of a drum 7 (the reference numerals designating their subjects generally). The drum 7 is mounted on a shaft 9 connected by bearings 11 to a support 13. As shown in FIG. 4, the drum includes a circular wall 15 connected to the shaft 9 for conjoint rotation therewith. The shaft 9 is rotatably driven by a suitable motor or line shaft (not shown) in a counter-clockwise direction in the illustrated embodiment of FIG. 1. The circular wall 15 cantilevers the forming surface 5 and the opposite side of the drum 7 is open. A vacuum duct 17 located radially inward of the forming surface 5 extends over an arc of the drum interior. The vacuum duct 17 has an arcuate, elongate entrance opening 19 under the foraminous forming surface 5, as will be described in more detail hereinafter, for fluid communication between the vacuum duct and the forming surface. The vacuum duct 17 is mounted on and in fluid communication with a vacuum conduit 21 connected to a vacuum source 23 (represented diagrammatically in FIG. 4). The vacuum source 23 may be, for example, an exhaust fan.

The vacuum duct 17 is connected to the vacuum supply conduit 21 along an outer peripheral surface of the conduit and extends circumferentially of the conduit. The vacuum duct 17 projects radially out from the vacuum conduit 21 toward the forming surface 5 and includes laterally spaced side walls 17A and angularly spaced end walls 17B. The shaft 9 extends through the wall 15 and into the vacuum supply conduit 21 where it is received in a bearing 25 within the conduit. The bearing 25 is sealed with the vacuum supply conduit 21 so that air is not drawn in around the shaft 9 where it enters the conduit. The vacuum duct 17 and conduit 21 are supported by an overhead mount 29.

A drum rim 31 is mounted on the wall 15 of the drum 7 and has a multiplicity of holes over its surface area to provide a substantially free movement of fluid, such as air, through the thickness of the rim. The rim 31 is generally tubular in shape and extends around the axis of rotation of the shaft 9 near the periphery of the wall 15. The rim 31 is cantilevered away from the drum wall 15, and has a radially inward-facing surface positioned closely adjacent to the entrance opening 19 of the vacuum duct 17. To provide an air resistant seal between the rim 31 and the entrance opening 19 of the vacuum duct 17, rim seals 33 are mounted on the inward-facing surface of the rim 31 for sliding, sealing engagement with the walls 17A of the vacuum duct. Seals (not shown) are also mounted on the end walls 17B of the vacuum duct 17 for sliding, sealing engagement with the inward-facing surface of the rim 31. The seals may be formed of a suitable material such as felt to permit the sliding, sealing engagements.

The apparatus 1 further comprises a forming chamber 41 through which the forming surface 5 is movable conjointly with the drum 7 upon rotation thereof. The forming chamber 41 is defined by a front wall 43, a rear wall 45 and opposed side walls 47 (only one of which is shown in FIGS. 1 and 2) assembled together and configured in a conventional manner to define an interior volume to which the forming surface 5 is exposed upon movement of the forming surface within the forming chamber. More particularly, in the illustrated embodiment the forming surface 5 moves in a counter-clockwise direction along an arcuate path P within the forming chamber 41 generally from an entrance 51 through which the forming surface enters the forming chamber substantially free of fibrous material, to an exit 53 through which the forming surface exits the forming chamber with the absorbent member formed thereon. Alternatively, the drum 7 may rotate in a clockwise direction relative to the forming chamber 41. The path P of movement of the forming surface 5 within the forming chamber 41 has a length defined by the arc of the forming surface extending from the entrance 51 to the exit 53 of the forming chamber. For example, in the illustrated embodiment the length of the forming path P is approximately two-thirds of the total outer circumference of the drum 7 and corresponds to an angle of about 240 degrees.

A conventional source of fibrous material, such as a fiber supply reservoir (not shown) or a fiberizer 55 delivers a fluent fibrous material (e.g., a flow of discrete fibers) into the forming chamber 41. The fiberizer 55 shown in FIGS. 1 and 2 is operatively positioned above the forming chamber 41 and can be a rotary hammer mill or a rotatable picker roll. However, it is to be understood that the fiberizer 55 may instead be located remote from the forming chamber 41 and that fluent fibrous material may be delivered to the interior of the forming chamber in other ways by other suitable devices and remain within the scope of the present invention. As an example, suitable fiberizers are available from Paper Converting Machine Company, a business having offices located in Green Bay, Wis., U.S.A.

The fibrous material may include natural fibers, synthetic fibers and combinations thereof. Examples of natural fibers include cellulosic fibers (e.g., wood pulp fibers), cotton fibers, wool fibers, silk fibers and the like, as well as combinations thereof. Synthetic fibers can include rayon fibers, polyolefin fibers, polyester fibers and the like, and combinations thereof. The fibrous material employed in the apparatus of FIG. 1 is derived from a batt B of wood pulp cellulose fibers fed to the fiberizer 55 wherein the fiberizer converts the batt into discrete fibers and delivers fluidized fibrous material into the interior of the forming chamber 41.

Other fibrous or particulate material for forming the absorbent member 3 may additionally be delivered into the forming chamber 41. For example, particles or fibers of superabsorbent material may be introduced into the forming chamber 41 by employing conventional mechanisms such as pipes, channels, spreaders, nozzles and the like, as well as combinations thereof. In the illustrated embodiment, superabsorbent material is delivered into the forming chamber 41 by delivery conduit and nozzle system (which is shown schematically in FIG. 1 and indicated at 57). Superabsorbent materials are well known in the art, and are readily available from various suppliers. For example, FAVOR SXM 880 superabsorbent is available from Stockhausen, Inc., a business having offices located in Greensboro, N.C., U.S.A.; and DRYTECH 2035 superabsorbent is available from Dow Chemical Company, a business having offices located in Midland, Mich., U.S.A. The fibers, particles and other desired material may be entrained in any suitable fluid medium within the forming chamber 41. Accordingly, any reference herein to air as being the entraining medium should be understood to be a general reference which encompasses any other operative entraining fluid.

The forming chamber 41 is supported by a suitable support frame (not shown) which may be anchored and/or joined to other suitable structural components as necessary or desirable. The forming surface 5 is illustrated herein as being part of the forming drum 7, but it is to be understood that other techniques for providing the forming surface 5 may also be employed without departing from the scope of the present invention. For example, the forming surface 5 may be provided by an endless forming belt (not shown). A forming belt of this type is shown in U.S. Pat. No. 5,466,409, entitled FORMING BELT FOR THREE-DIMENSIONAL FORMING APPLICATIONS by M. Partridge et al. which issued on Nov. 14, 1995.

The foraminous forming surface 5 is defined in the illustrated embodiment by a series of form members 61 which are arranged end-to-end around the periphery of the forming drum 7 and independently attached to the drum. As may be seen in FIG. 3, the form members 61 each define a substantially identical mold or pattern 63 in which fibrous material is collected. The patterns 63 correspond to a desired shape of individual absorbent members 3 which repeats over the circumference of the drum 7. However, partially repeating or non-repeating pattern shapes may be used with the present invention. It is also understood that a continuous, un-patterned absorbent member may be formed on the forming surface, such as where the forming surface is flat or where the formed absorbent member is generally rectangular, and is subsequently processed (e.g., cut or otherwise formed) to a desired shape.

Figure 11:
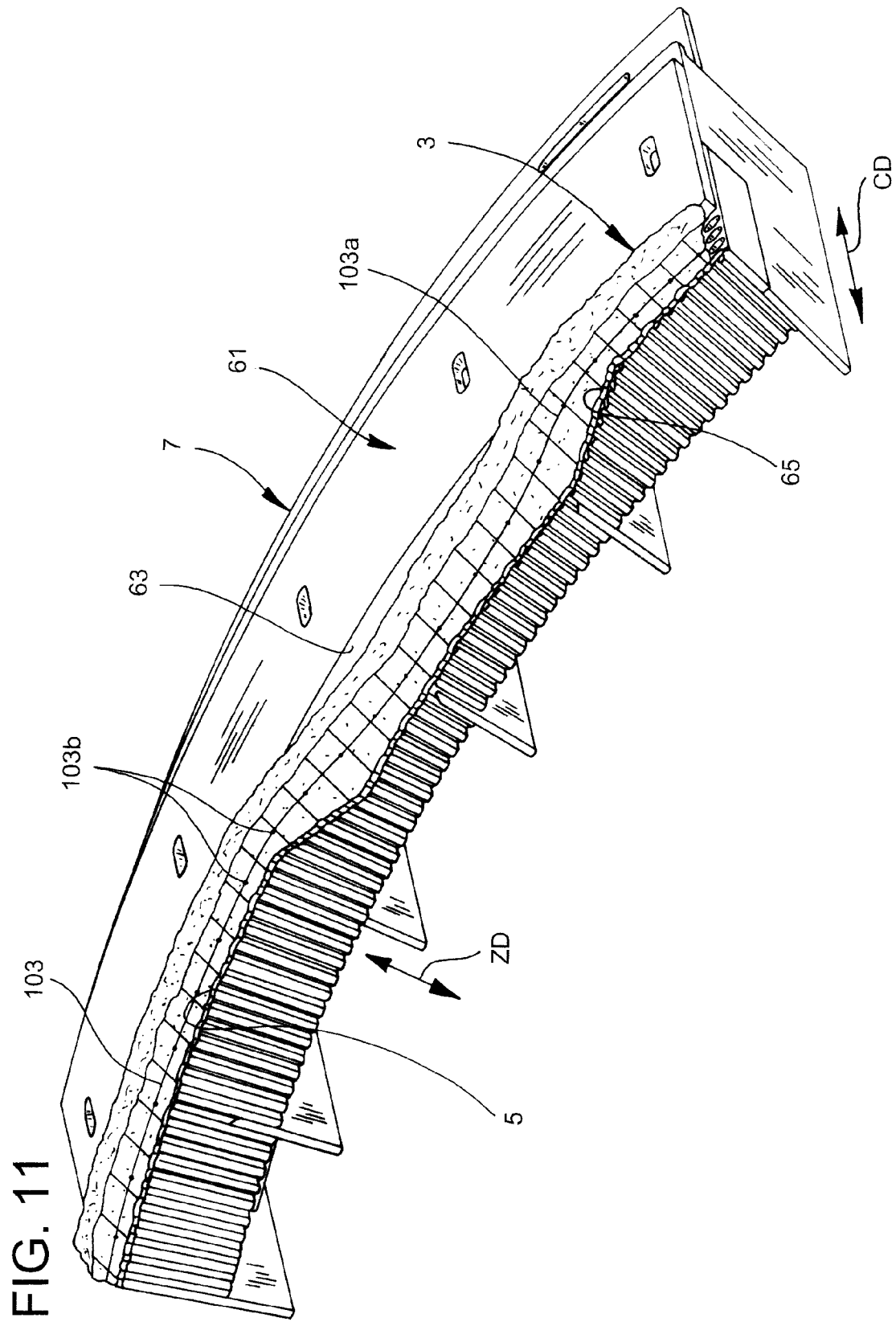
FIG. 11 is a perspective section of a portion of the forming drum of FIG. 3 with a reinforced absorbent member being formed on the drum.
Figure 12:
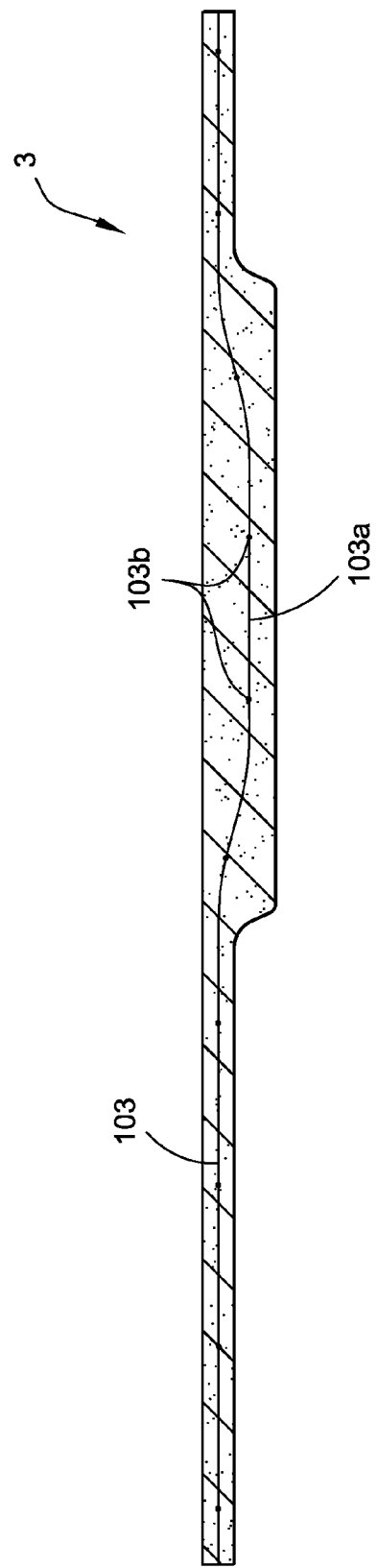
FIG. 12 is a longitudinal cross-section of an absorbent member formed in the apparatus of FIG. 1.

As best seen in FIG. 11, the pattern 63 of the illustrated embodiment has a non-uniform depth, or thickness, along its length. More particularly, the forming surface has a central pocket 65 so that that an absorbent member formed on the forming surface 5 varies in thickness (e.g., in the Z-direction) as shown in FIGS. 11 and 12. However, the pattern 63 defined at least in part by the form members 61 may alternatively be of a uniform depth without departing from the scope of this invention. It is also understood that the depth of the pattern 63 may also, or may instead, be non-uniform across all or part of the width of the pattern.

In operation, the vacuum source 23 (FIG. 4) creates a vacuum in the vacuum duct 17 relative to the interior of the forming chamber 41. As the forming surface 5 enters and then moves through the forming chamber 41 along the forming path P toward the exit 53 of the chamber, the fluidized fibrous materials and other particles within the forming chamber are operatively carried or transported by an entraining air stream and drawn inward by the vacuum toward the foraminous forming surface 5. Air passes inward through the forming surface 5 and is subsequently passed out of the drum 7 through the vacuum supply conduit 21. Fibers and other particulates are collected by the forming surface 5 as the air passes therethrough such that the collection of fibrous material forms an absorbent member 3 on the forming surface.

Subsequently, the drum 7 carrying the absorbent member 3 passes out of the forming chamber 41 through the exit 53 to a scarfing system, generally indicated at 71 in FIG. 1, where excess thickness of the absorbent member can be trimmed and removed to a predetermined extent. The scarfing system 71 includes a scarfing chamber 73 and a scarfing roll 75 positioned within the scarfing chamber. The scarfing roll 75 abrades excess fibrous material from the absorbent member 3, and the removed fibers are transported away from the scarfing chamber 73 within a suitable discharge conduit (not shown), as is well known in the art. The removed fibrous material may, for example, be recycled back into the forming chamber 41 or the fiberizer 55, as desired. Additionally, the scarfing roll 75 can rearrange and redistribute the fibrous material along the machine-direction MD of the absorbent member 3 and/or along the lateral or cross-machine direction CD of the absorbent member.

The rotatable scarfing roll 75 is operatively connected and joined to a suitable shaft member (not shown), and is driven by a suitable drive system (not shown). The drive system may include any conventional apparatus, such as a dedicated motor, or a coupling, gear or other transmission mechanism operatively connected to the motor or drive mechanism used to rotate the forming drum 7. The scarfing roll system 71 can provide a conventional trimming mechanism for removing or redistributing any excess thickness of the absorbent member 3 that has been formed on the forming surface 5. The scarfing operation can yield an absorbent member 3 having a selected contour on a major face-surface thereof that has been contacted by the scarfing roll 75. The surface of the scarfing roll 75 can be adjusted to provide a desired contour along the scarfed surface of the absorbent member 3. In the illustrated embodiment, the scarfing roll 75 can, for example, be configured to provide a substantially flat surface along the scarfed surface of the absorbent member 3. The scarfing roll 75 can optionally be configured to provide a non-flat surface. The scarfing roll 75 is disposed in spaced adjacent relationship to the forming surface 5, and the forming surface is translated past the scarfing roll upon rotation of the drum 7.

In the illustrated embodiment, the scarfing roll 75 rotates in the same direction (e.g., counter-clockwise) as the drum 7 to remove fibrous material from the absorbent member in a direction counter to the direction of movement (e.g., the machine direction MD) of the absorbent member with the drum. Alternatively, the scarfing roll 75 may be rotated in the opposite direction (e.g., clockwise) of the forming drum 7 rotation. In either instance, the rotational speed of the scarfing roll 75 should be suitably selected to provide an effective scarfing action against the contacted surface of the formed absorbent member 3. In like manner, any other suitable trimming mechanism may be employed in place of the scarfing roll system 71 to provide a cutting or abrading action to the fibrous absorbent member 3 by a relative movement between the absorbent member and the selected trimming mechanism.

After the scarfing operation, the portion of the forming surface 5 on which the absorbent member 3 is formed can be moved to a release zone of the apparatus 1 disposed exterior of the forming chamber 41. In the release zone, the absorbent member 3 is drawn away from the forming surface 5 onto a conveyor, which is indicated generally at 81. The release can be assisted by the application of air pressure from the interior of the drum 7. The conveyor 81 receives the formed absorbent member 3 from the forming drum 7, and conveys the absorbent member to a collection area or to a location for further processing (not shown). Suitable conveyors can, for example, include conveyer belts, vacuum drums, transport rollers, electromagnetic suspension conveyors, fluid suspension conveyors or the like, as well as combinations thereof.

In the illustrated embodiment, the conveyor 81 includes an endless conveyor belt 83 disposed about rollers 85. A vacuum suction box 87 is located below the conveyor belt 83 to draw the absorbent member 3 away from the forming surface 5. The belt 83 is perforate and the vacuum box 87 defines a plenum beneath the portion of the belt in close proximity to the forming surface so that the vacuum within the vacuum box acts on the absorbent member 3 on the forming surface 5. Removal of the absorbent member 3 from the forming surface 5 can alternatively be accomplished by the weight of the absorbent member, by centrifugal force, by mechanical ejection, by positive air pressure or by some combination thereof or by another suitable method without departing from the scope of this invention.

The apparatus 1 and method described thus far for air forming a fibrous absorbent member 3 is generally conventional and well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other such apparatus are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, and U.S. patent application Ser. No. 09/947,128, entitled MULTI-STAGE FORMING DRUM COMMUTATOR by D. P. Murphy et al., filed Sep. 4, 2001 (now U.S. Pat. No. 6,630,096), the entire disclosures of which are incorporated herein by reference in a manner that is consistent herewith.

Examples of techniques for introducing a selected quantity of superabsorbent particles into a forming chamber 41 are described in U.S. Pat. No. 4,927,582 entitled METHOD AND APPARATUS FOR CREATING A GRADUATED DISTRIBUTION OF GRANULE MATERIALS IN A FIBER MAT by R. E. Bryson which issued May 22, 1990; the entire disclosure of which is incorporated herein by reference in a manner that is consistent herewith. Therefore, construction and operation of the apparatus 1 will not be further described herein except to the extent necessary to set forth the present invention.

Referring back to FIGS. 1 and 2, the forming chamber 41 of the apparatus 1 further comprises a delivery tube, generally indicated at 101, through which a reinforcing web 103 is introduced into the interior of the forming chamber for incorporation into the absorbent member 3. The reinforcing web 103 is desirably a continuous web constructed of a material which is sufficiently porous to permit entraining air flowing within the forming chamber 41 toward the forming surface 5 to pass therethrough. Even more desirably, the reinforcing web 103 is at least semi-permeable to the discrete fibers flowing within the forming chamber 41.

Figure 9:
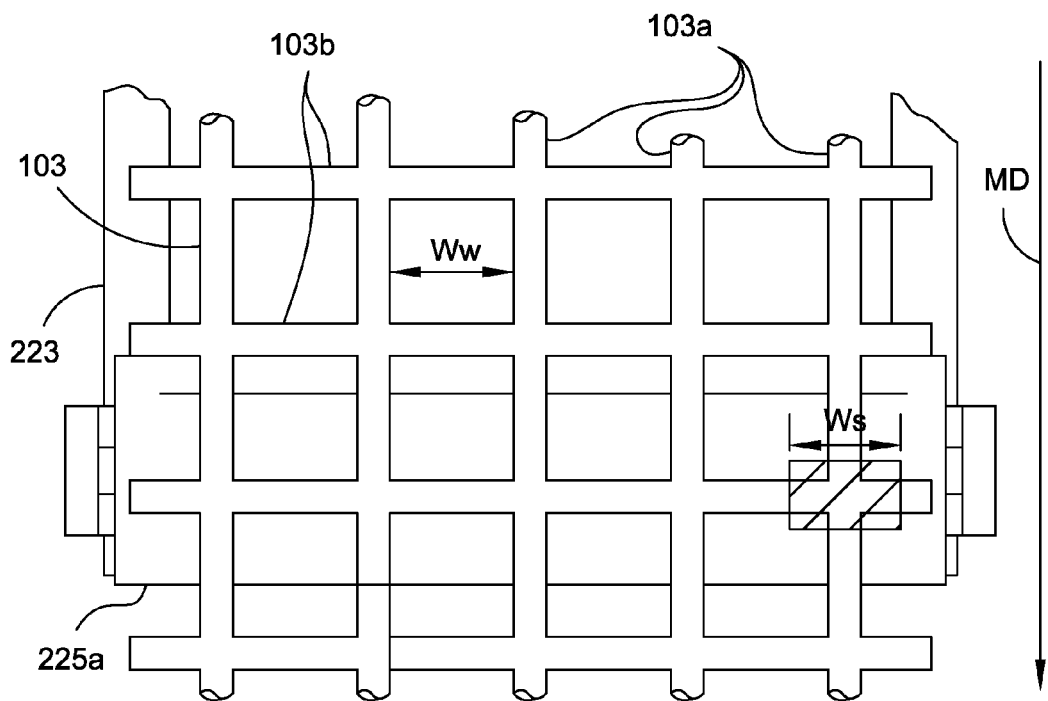
FIG. 9 is an enlarged top view of a portion of the control system of FIG. 8.

For example, the reinforcing web 103 of the illustrated embodiment is a scrim (e.g., netting or mesh material) formed from longitudinally (e.g., machine direction MD) and laterally (e.g., cross-machine direction CD) oriented filaments, respectively designated 103a and 103b in FIG. 9, arranged in a generally grid pattern and interconnected, such as by being bonded, at intersecting points to form an open mesh (i.e., having a plurality of generally rectangular or square-shaped openings) through which the fluent fibrous material in the forming chamber may permeate. Alternatively, the scrim filaments 103a, 103b may be oriented other than in a longitudinal or lateral orientation so as to define openings which are other than rectangular or square-shaped, such as diamond shaped, triangular shaped or other suitably shaped openings.

In one embodiment, the openings defined by the filaments 103a, 103b of the scrim are sufficiently sized relative to the discrete fibers flowing within the forming chamber 41 to facilitate entanglement of fibers with the scrim upon entry of the scrim into the forming chamber. As an example, the longitudinally oriented filaments 103a are laterally spaced from each other a distance of about 2 mm to about 30 mm and the laterally oriented filaments 103b are longitudinally spaced from each other a distance of about 2 mm to about 30 mm. The width of the scrim is desirably about 25 percent to about 100 percent of the width of the absorbent member 3, more desirably about 25 percent to about 75 percent, and even more desirably about 50 percent to about 75 percent. As a further example, the width of the scrim may be in the range of about 20 mm to about 400 mm.

The scrim filaments 103a, 103b can be constructed of a transparent, or at least translucent, material so as to be generally invisible when the absorbent member 3 incorporating the scrim is incorporated into an article such as a diaper, training pants, etc. The scrim may optionally be white so as to be generally invisible but still optically detectable by suitable detection apparatus, or it may be colored for visibility to the consumer. The scrim is often formed with the laterally oriented filaments 103b projecting laterally out beyond the outermost longitudinally oriented filaments 103a as shown in FIG. 9. However, it is understood that the scrim may be laterally bounded by the outermost longitudinally oriented filaments 103a without departing from the scope of this invention. It is also contemplated that the reinforcing web 103 may instead comprise an apertured or perforated film, an air permeable woven or non-woven web, or another suitable material without departing from the scope of this invention.

While not shown in the drawings, it is contemplated that the scrim may also comprise a single longitudinally oriented filament 103a with one or more laterally oriented filaments 103b, or barbs, extending out from the longitudinally oriented filament in longitudinally spaced relationship with each other. It is also contemplated that the scrim may comprise two or more discrete or otherwise unconnected longitudinally oriented filaments 103a, e.g., in laterally spaced relationship with each other, with each longitudinally oriented filament having respective laterally oriented filaments 103b or barbs extending outward therefrom in longitudinally spaced relationship with each other. Suitable absorbent members 3 which incorporate scrim as a reinforcing web 103 are disclosed in co-assigned U.S. patent application Ser. No. 10/306,086 entitled "Absorbent Article with Reinforced Absorbent Structure," filed Nov. 27, 2002 by David W. Heyn et al. (attorney docket no. K-C 16,836).

The delivery tube 101 extends through and is supported by the front wall 43 of the forming chamber 41 and has a central passage 105 extending from an inlet end 107 of the tube disposed exterior of the forming chamber to a discharge end 109 disposed within the forming chamber in generally adjacent, radially spaced relationship with the forming surface 5 on which the absorbent member 3 is formed. The inlet end 107 of the delivery tube 101 is open to the exterior of the forming chamber 41 for receiving the reinforcing web 103 into the central passage 105 of the tube and into the forming chamber. The portion of the delivery tube 101 adjacent the discharge end 109 thereof extends within the forming chamber to shield the web against contact by fibrous material within the forming chamber until the web reaches the discharge end of the tube. The discharge end 109 is open to the interior of the forming chamber 41 and broadly defines an opening in the forming chamber through which the reinforcing web 103 is introduced into the interior of the forming chamber and exposed to the fluent fibrous material.

It is contemplated that the discharge end 109 of the delivery tube 101 may be flush with the front wall 43 of the forming chamber 41 instead of extending into the interior volume thereof, or that the inlet end 107 of the tube may be flush with the forming chamber wall, or that the delivery tube may be omitted altogether such that the reinforcing web 103 simply enters the forming chamber through an opening formed in the front wall (or other wall) of the forming chamber, without departing from the scope of this invention. A conventional unwind 111 supports a supply roll 113 of reinforcing web 103 (broadly, a source of reinforcing web) exterior of the forming chamber 41 and a guide assembly, generally indicated at 115, is positioned intermediate the unwind and the inlet end 107 of the delivery tube 101 for guiding the reinforcing web into the tube.

As shown in FIGS. 1 and 2, the delivery tube 101 is desirably oriented to extend longitudinally other than radially relative to the forming drum 7 for reasons which will be described later herein. For example, in the illustrated embodiment the delivery tube 101 is angled upward relative to the front wall 43 of the forming chamber 41 and, more particularly, the longitudinal axis of the tube is oriented at angle of about 90 degrees to about 270 degrees relative to a radial line R (FIG. 2) extending from the center of the drum 7 to the discharge end 109 of the tube 101. The tube 101 is also oriented with its discharge end 109 facing generally in the direction of movement of the forming surface 5. It is understood, however, that the delivery tube 101 may be oriented with its discharge end 109 facing in a direction generally counter to the direction of movement of the forming surface 5. It is also contemplated that the tube 101 may instead be oriented to extend radially relative to the forming drum 7 (e.g., co-linear with the radius of the drum) without departing from the scope of this invention.

The delivery tube 101 of the illustrated embodiment is constructed of substantially clear polycarbonate to permit the operator to visually monitor the alignment and movement of the reinforcing web 103 within the central passage 105 of the tube during operation of the apparatus 1. However, the tube 101 may alternatively be constructed of other suitable materials, such as steel or other metals, plastics and the like. As seen best in FIG. 6, the delivery tube 101 is diamond-shaped in cross-section to provide a generally aerodynamic profile within the forming chamber 41 to thereby inhibit fibrous material against accumulating on the outer surface of the tube and to minimize any disruption of the air and fiber flow within the forming chamber. It is contemplated, however, that the cross-section of the delivery tube 101 may be substantially of any shape, including circular, polygonal, tear-drop, airfoil or other suitable shape. A generally flat panel 117 laterally spans the central passage 105 of the delivery tube 101 and extends longitudinally from the inlet end 107 to the discharge end 109 of the tube. However, it is contemplated that the panel 117 may extend only partially along the length of the tube 101 as long as the panel terminates at or generally adjacent the discharge end of the tube.

Figure 6:
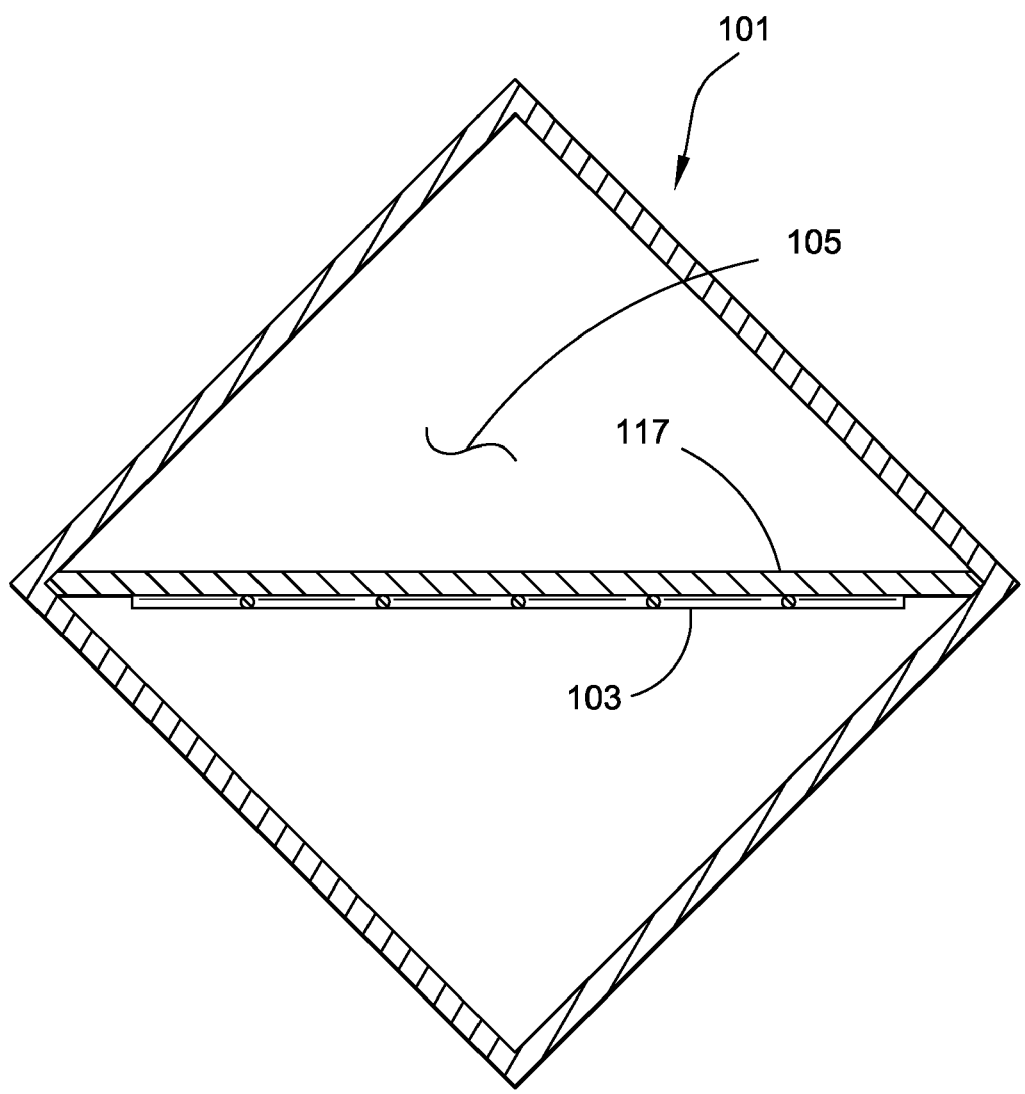
FIG. 6 is a cross-section taken in the plane of line 6-6 of FIG. 5.

The width of the panel 117, and hence the cross-sectional width of the delivery tube 101, is slightly greater than the width of the reinforcing web 103 to inhibit impacting, folding or otherwise bunching of the web against the side of the tube. However, the panel 117 width is desirably sufficiently limited to inhibit cross-directional CD misalignment of the reinforcing web 103 relative to the absorbent member 3 as the web passes from the discharge end 109 of the delivery tube 101 toward the forming surface 5. For example, the panel 117 width (and cross-sectional width of the delivery tube 101) is desirably in the range of about 0.1 percent to about 35 percent greater than the width of the reinforcing web 103. In the illustrated embodiment the width of the reinforcing web 103 as shown in FIG. 6 is about 52 mm and the width of the panel 117 and cross-sectional width of the tube 101 is about 68 mm (e.g., about 31 percent greater than the width of the reinforcing web). As an additional example, the absorbent member into which the reinforcing web is incorporated has a width of approximately 76 mm during its formation within the forming chamber 41. The vacuum within the forming chamber 41 generally draws the reinforcing web 103 through the central passage 105 of the delivery tube 101 to the discharge end 109 thereof and then over the end of the panel 117 toward the forming surface to incorporate the reinforcing web into the absorbent member 3 being formed on the forming surface.

To make a reinforced fibrous absorbent member, fluidized fibrous material is introduced into the forming chamber 41 and collected on the forming surface 5 (e.g., as a result of the fibrous material being drawn by the vacuum to the forming surface) as the forming surface moves within the forming chamber from the entrance 51 to the exit 53 thereof as described previously. Concurrently, the vacuum draws the reinforcing web 103 through the delivery tube 101 from its inlet end 107 to its discharge end 109 and then over the end of the panel 117 toward the forming surface 5. To initiate movement of the reinforcing web 103 within the delivery tube 101, a piece of tape (not shown) is adhered to the leading edge of the reinforcing web 103 to close some of the openings adjacent the leading edge. The leading end of the web 103 is then manually unwound from the supply roll 113 and fed into the inlet end 107 of the delivery tube 101 whereby the web is more easily drawn by the vacuum through the tube into the forming chamber 41 and toward the forming surface 5. In this manner, the web is essentially self-threading in the sense that no additional mechanical apparatus is required to initially thread the web into the forming chamber 41.

It is also contemplated that instead of the vacuum drawing the reinforcing web 103 through the tube 101 and into the forming chamber 41, or in addition thereto, the reinforcing web may be drawn into the forming chamber mechanically by a suitable drive system (not shown), or the web may be delivered through the tube into the forming chamber by a motive (e.g., positive pressure) air flow (not shown) or by a suitable mechanical drive system (not shown) disposed exterior of the forming chamber.

The portion of the delivery tube 101 adjacent the discharge end 109 and extending within the interior of the forming chamber 41 shields the reinforcing web 103 from the fibrous material until the web reaches the discharge end of the tube. Fibrous material instead passes around the delivery tube 101 toward the forming surface 5 so that the flow of fibrous material to the forming surface is substantially uniform or otherwise free or uninterrupted and can form the lower portion of a partially formed absorbent member 3.

As the reinforcing web 103 traverses the distance from the discharge end 109 of the delivery tube 101 to the forming surface 5, the opposite (e.g., inner and outer) surfaces of the reinforcing web are exposed to the fluent fibrous material within the forming chamber. While some fibrous material permeates through the reinforcing web 103, the size of the web openings relative to the discrete fluidized fibers of the fibrous material promotes entanglement of the fibers with the web. For example, the fibers may become entangled with the web 103 by inter-weaving with the web filaments 103a, 103b or by wrapping around the filaments. The force of the vacuum is believed to provide the impetus for the entangling action of the fibers. In addition, those fibers entangled with the web 103 may also become entangled with other fibers, further promoting structural unification of the fibers and web. The reinforcing web 103, with fibrous material entangled therewith, is then laid over the forming surface 5, and more particularly it is laid over the partially formed absorbent member 3, to move conjointly with the absorbent member along the path P of movement of the forming surface.

Entanglement of the fibrous material with the reinforcing web 103 before the web overlays the partially formed absorbent member facilitates drawing of the reinforcing web by the vacuum toward the forming surface 5 to thereby conform the reinforcing web generally to the contour of the forming surface, and more particularly to the contour of the partially formed absorbent member as shown in FIG. 11. However, it is understood that the web 103 may be sufficiently tensioned upon delivery into the forming chamber 41 to inhibit the web against conforming to the forming surface 5 contour whereby upon a change in depth of the forming surface, the web instead spans the depth change (e.g., the pocket 65 in FIG. 11) in a chord-like manner.

Upon further movement of the forming surface 5 within the forming chamber 41 toward the exit 53, additional fibrous material is drawn toward the forming surface and collects on the partially formed absorbent member 3 and reinforcing web 103 to further increase the thickness of the absorbent member and to enclose or otherwise secure the reinforcing web therein as shown in FIG. 11. Where the reinforcing web 103 is scrim as in the illustrated embodiment, the additional fibrous material collects within and becomes entangled with the reinforcing web and/or with the fibrous material previously entangled with the web to further secure the web within the absorbent member 3. The entanglement of the fibrous material is desirably sufficient such that the scrim cannot be removed from the absorbent member without fibrous material being removed along with the scrim.

The Z-direction ZD position of the reinforcing web 103 within the thickness of the absorbent member 3 is generally a function of the position of the discharge end 109 of the delivery tube 101 along the forming path P of the forming surface 5 and the variations in depth of the forming surface. For example, approximately 80%-90% of the absorbent member 3 thickness is formed within about the first 50% of the forming path P. It is understood, however, that this may vary depending on the rotational speed of the drum 7 and the flow rate of the fluent fibrous material within the flow chamber 41.

Desirably, the reinforcing web is positioned within a range of about 5% to about 95% of the thickness of the absorbent member. For an absorbent member 3 of non-uniform thickness, the reinforcing web 103 is more desirably located within a range of about 5% to about 75% of the thickness of the absorbent member, and more desirably within the range of about 25% to about 75% of the thickness of the absorbent member.

The discharge end 109 of the delivery tube 101 is desirably at a position relative to the path P downstream of the forming chamber entrance 51 such that the reinforcing web 103 overlays the partially formed absorbent member 3 at a distance downstream of the forming chamber entrance in the range of about 5% to about 66% of the total length of the path. More particularly, for an absorbent member of non-uniform thickness such as shown in FIGS. 11 and 12, the discharge end 109 of the delivery tube 101 is more desirably positioned such that the reinforcing web overlays the absorbent member 3 a distance downstream of the forming chamber entrance 51 in the range of about 5% to about 25% of the total length of the path P so as to position the reinforcing web 103 generally centrally within the thickness (e.g., in the Z-direction ZD) of the absorbent member 3, and more desirably in the range of about 10% to about 25%. Because the depth of the forming surface 5 varies, the Z-direction ZD placement of the reinforcing web 103 within the absorbent member may also vary.

For an absorbent member 3 of generally uniform thickness, the discharge end 109 of the delivery tube 101 is more desirably positioned such that the reinforcing web 103 overlays the partially formed absorbent member 3 at a distance downstream of the forming chamber entrance 51 in the range of about 20% to about 66% of the total length of the path P, and more desirably in the range of about 20% to about 40%. It is understood, however, that the discharge end 109 of the delivery tube 101 may be positioned generally anywhere along the forming path P of the forming surface 5 downstream of the forming chamber entrance 51, including beyond 66% of the total length of the forming path, to locate the reinforcing web 103 at generally any Z-direction ZD position within the thickness of the absorbent member 3, as long as the reinforcing web is sufficiently positioned within the absorbent member so as to not interfere with operation of the scarfing roll 75 to remove fibrous material from the absorbent member.

It is therefore understood that the delivery tube 101 may extend other than through the front wall 43 of the forming chamber 41 and may extend generally at any angle relative to the radius of the forming drum 7 to position the discharge end 109 of the delivery tube at the desired position and orientation along the forming path P of the forming surface 5 and remain within the scope of this invention.

The span, or distance, that the reinforcing web 103 traverses in generally open space within the forming chamber 41 as the web travels from the discharge end 109 of the delivery tube 101 toward the forming surface 5 is at least partially a function of the radial spacing between the discharge end of the tube and the forming surface 5. Increasing this distance exposes the inner and outer surfaces of the reinforcing web 103 to the fluent fibrous material in the forming chamber 41 for a longer duration before the web is deposited onto the forming surface 5, or more particularly the absorbent member 3. Where the reinforcing web 103 is scrim, increasing this distance facilitates increased entanglement of the fibrous material with the scrim prior to the scrim being laid over the forming surface 5, and more particularly over the absorbent member 3.

However, this distance is desirably sufficiently small to inhibit fluttering, bending or otherwise cross-machine direction CD and/or Z-direction ZD misalignment of the reinforcing web 103 within the forming chamber 41. Otherwise, the reinforcing web 103 may not properly overlay the partially formed absorbent member and thus stick out the side of the absorbent member or be located at an undesirable depth within the absorbent member. As an example, the discharge end 109 of the delivery tube 101 is desirably spaced radially from the forming surface 5 a distance such that the span of reinforcing web 103 exposed to fibrous material within the forming chamber 41 as the web traverses from the discharge end of the tube onto the partially formed absorbent member 3 is in the range of about 1 cm to about 100 cm, more desirably in the range of about 1 cm to about 50 cm, still more desirably in the range of about 1 cm to about 20 cm and most desirably in the range of about 1 cm to about 10 cm.

Figure 5:
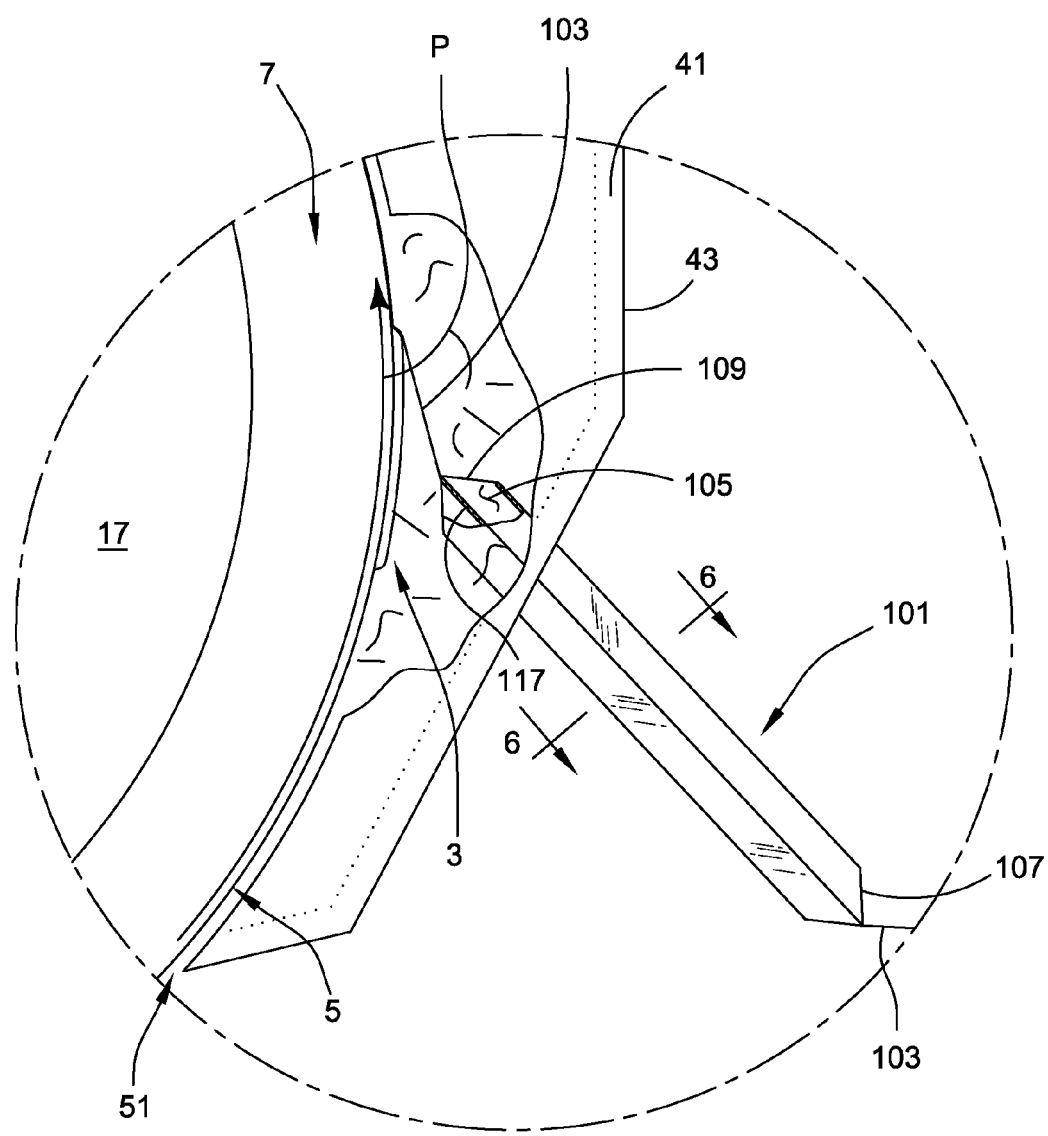
FIG. 5 is an enlarged side elevation of the circled portion of the apparatus of FIG. 2.

In the illustrated embodiment, the reinforcing web 103 passes through the delivery tube 101 within the lower half of the central passage 105 to generally ride on the lower surface of the panel 117 as shown in FIG. 5. Upon reaching the discharge end 109 of the delivery tube 101, the reinforcing web 103 is drawn over the end of the panel 117 toward the forming surface 5 to reduce the risk of lateral folding or bunching of the web and to slightly tension the web to promote the web lying flat on the absorbent member 3. Where the drum 7 instead rotates clockwise, the reinforcing web 103 desirably passes through the tube within the upper half of the central passage 105 and over the end of the panel 117 toward the forming surface 5.

As the drum 7 carrying the reinforced absorbent member 3 passes out of the forming chamber 41 through the exit 53 to the scarfing system 71, excess thickness is removed from the outer face of the absorbent member. For example, in the illustrated embodiment the scarfing system 71 removes sufficient thickness from the outer face of the absorbent member 3 so that the outer face becomes generally flat as shown in FIG. 12. As a result, the position of the reinforcing web 103 within the thickness of the reinforced absorbent member 103 is more noticeably non-uniform along at least a portion of the length of the absorbent member.

Figure 13:
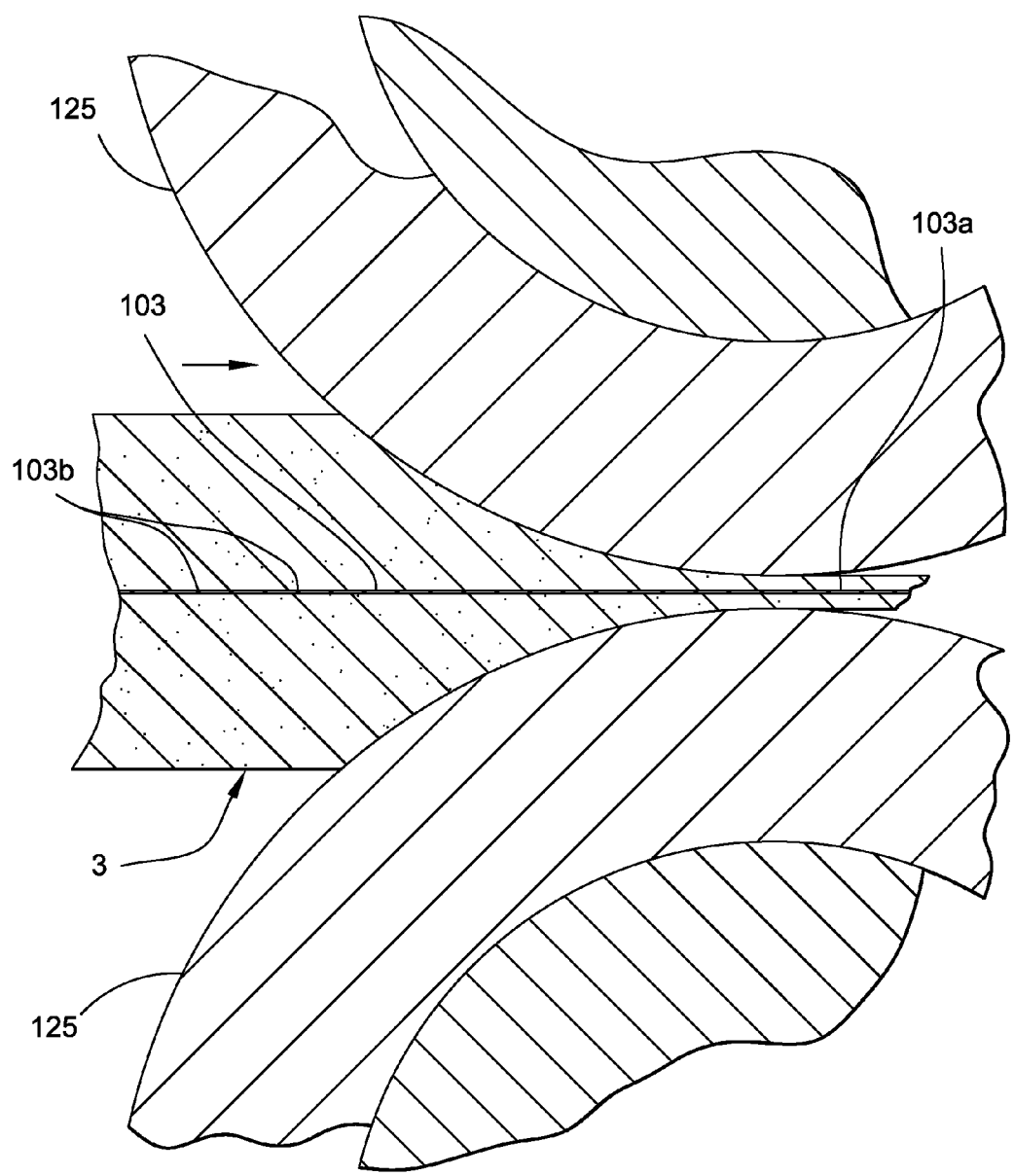
FIG. 13 is a schematic section of a reinforced absorbent member passing through debulking rollers.

It will be readily apparent that various additional devices and techniques can be employed to further process the absorbent member 3 once it exits the forming chamber 41. For example, the absorbent member 3 can be compressed at a debulking station comprising debulking rollers 125 as shown in FIG. 13. Entanglement of the fibers with the reinforcing web 103 may be further augmented by passing the reinforced absorbent member 3 through the debulking rollers 125. The debulking rollers 125 desirably define a nip which is considerably smaller than the thickness of the reinforced absorbent member 3. Thus, the absorbent member 3 is compressed and markedly reduced in thickness by operation of the debulking rollers 125. The fibers of the web 108 undergo considerable deformation when passing through the nip of the rollers 125, especially at high speeds and significant compression. It is believed that this action causes at least some additional fibers to be interwoven with and/or wrapped around the filaments 103a, 103b of the reinforcing web 103, thereby improving entanglement. Moreover, fibers already somewhat entangled with the filaments 103a, 103b can be further secured to the filaments.

In addition, various conventional devices and techniques can be employed to sever the absorbent member 3 into predetermined lengths to provide discrete air formed reinforced fibrous absorbent members. The severing system may, for example, include a die cutter, a water cutter, rotary knives, reciprocating knives, energy beam cutters, particle beam cutters or the like, as well as combinations thereof. After severing, the discrete absorbent members 3 can be transported and delivered for further processing operations, as desired.

With reference now to FIGS. 1 and 7-9, a control system for controlling the transverse (e.g., the cross-machine direction CD or otherwise lateral or widthwise) position of the reinforcing web 103 as the web is conveyed lengthwise (e.g., in the machine direction MD or otherwise longitudinally) is generally indicated at 201 and comprises the guide assembly 115. The guide assembly 115 of the illustrated embodiment is a conventional guide assembly capable of pivoting movement relative to the lengthwise conveyance of the web 103 generally in the plane of the web as indicated by the arcuate direction arrows illustrated FIG. 8. As an example, one suitable guide assembly 115 is available from Erhardt + Leimer Inc. of Spartanburg, S.C., U.S.A. under the model designation DRS 1202 DCS Narrow Web Pivot Guider.

The guide assembly 115 generally comprises a rectangular base 221 which is secured against movement and a rectangular frame 223 pivotally mounted on the base by suitable bearings (not shown) for pivoting movement relative to the base and the reinforcing web 103. Two idler rollers 225a, 225b are mounted for rotation on the frame 223 in parallel, spaced relationship with each other such that in an unpivoted position of the frame the rollers extend generally transverse to the lengthwise direction of conveyance of the reinforcing web 103. The reinforcing web 103 passes over the idler rollers 225a, 225b in contact therewith. It is understood, however, that the web 103 may pass under both rollers 225a, 225b, or may pass under one roller and over the other in a serpentine manner, as long as the web is contact with the rollers. As is known to those skilled in the art, pivoting movement of the frame 223 relative to the base 221 and web 103 urges the web to move transversely relative to the lengthwise direction of conveyance of the web in the direction that the frame is pivoted. The frame 223 is operably connected to a suitable drive motor (not shown) for driving pivoting movement of the frame on the base 221. A suitable controller (illustrated schematically in FIGS. 7 and 8 and indicated as 227), such as a digital position controller, is in electrical communication with the drive motor to permit selective adjustment of the transverse position of the reinforcing web 103.

Figure 7:
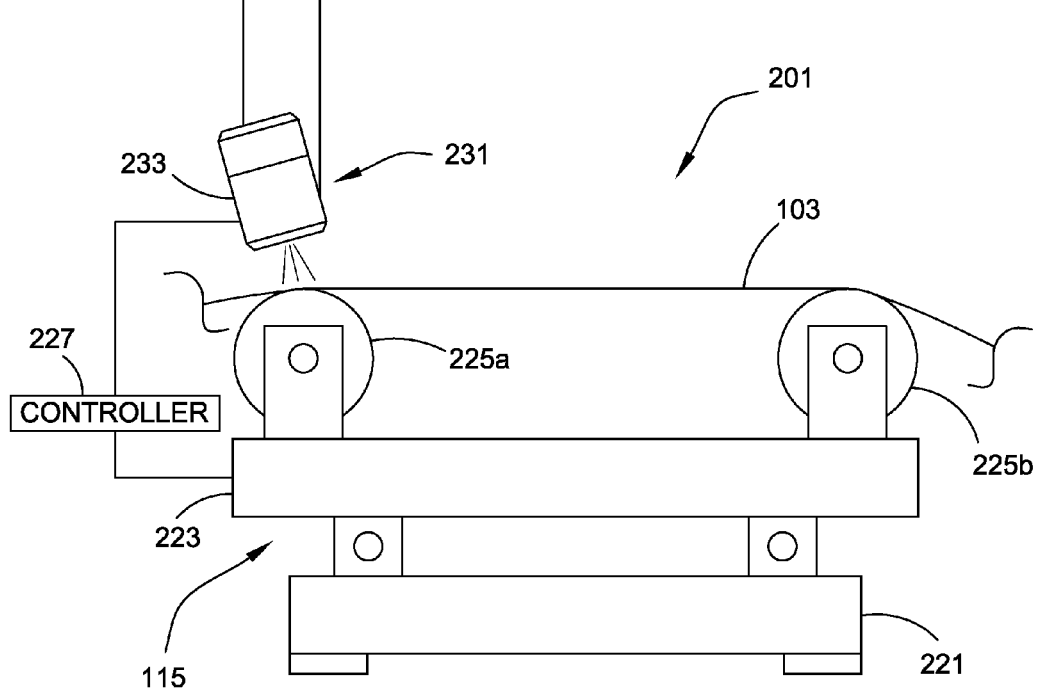
FIG. 7 is an enlarged side elevation of a control system for controlling the transverse position of a reinforcing web during lengthwise conveyance of the web.
Figure 8:
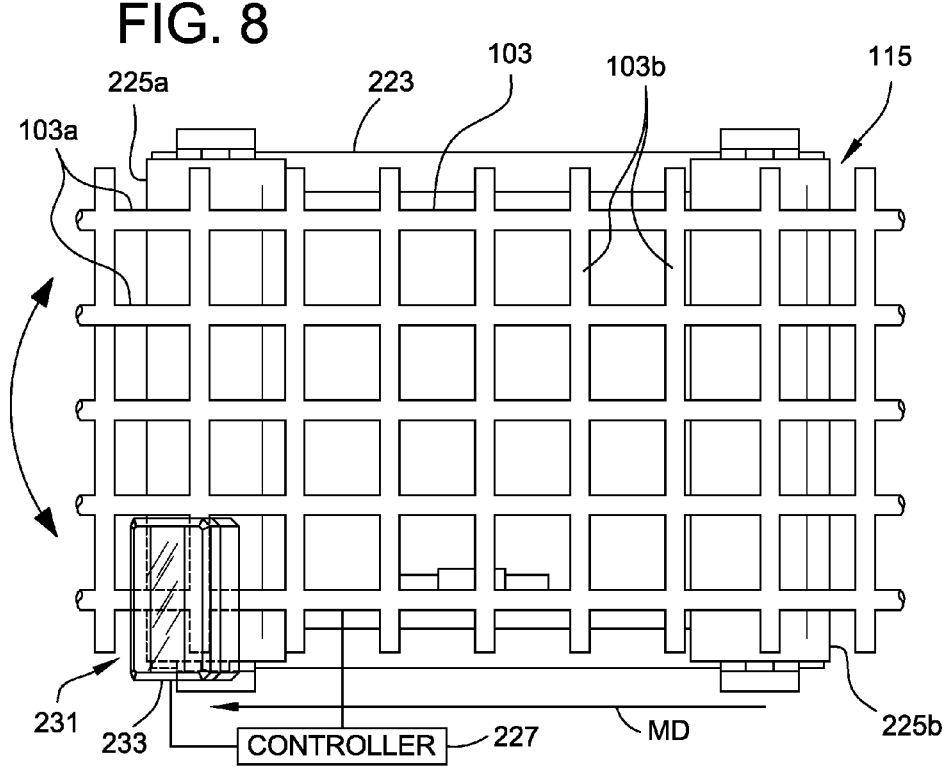
FIG. 8 is a top view of the control system of FIG. 7.

The control system 201 further comprises an inspection device, generally indicated at 231, for intermittently or continuously inspecting the reinforcing web 103 to determine the transverse position thereof as the web is conveyed lengthwise from the supply roll 113 to the inlet end 107 of the delivery tube 101. In the illustrated embodiment, the inspection device 231 is an optical sensor 233 positioned above one idler roller 225a of the guide assembly 115 in spaced relationship therewith and at a transverse position relative the web 103 that corresponds generally to a target (e.g., desired or predetermined) transverse position of one of the longitudinally oriented filaments 103a of the reinforcing web. For example, the sensor 233 shown in FIGS. 7 and 8 is positioned approximately 24±2 mm above the idler roller 225a and is oriented generally at an angle relative to the lengthwise direction of conveyance of the web 103, such as about 14±2 degrees. It is contemplated that the sensor 233 may instead be positioned adjacent the other idler roller 225b, or at a location between the idler rollers, or at a location upstream or downstream of the guide assembly 115 without departing from the scope of this invention.

One suitable optical sensor 233 is available from Erhardt + Leimer Inc. of Spartanburg, S.C., U.S.A. under the model designation FE 5002. Color Line Sensor. The optical sensor 233 irradiates (e.g., in the illustrated embodiment, illuminates) the reinforcing web 103 as the web passes beneath the sensor and senses radiation (e.g., light in the illustrated embodiment) reflected by the web and the outer surface of the idler roller 225a (broadly considered herein as a background member for the web) to determine the transverse position of the longitudinally oriented filament being monitored based on the contrast in radiation reflected by the web and the outer surface of the roller. Construction and operation of such an optical sensor 233 is known in the art and therefore will not be further described herein except to the extent necessary to set forth the present invention.

As described previously, the reinforcing web 103 of the illustrated embodiment is a scrim comprising filaments 103a, 103b constructed of a transparent, or at least translucent material. Since most of the scrim 103 is open space (e.g., the mesh openings) and the filaments 103a, 103b are translucent, the idler roller 225a (e.g., the background member) must be sufficiently dark in color to provide a highly contrasted background to the translucent filaments. More particularly, the idler roller 225a is desirably constructed of a black carbon material to provide a black background to the scrim filaments 103a, 103b. It is understood, however, that the idler roller 225a may be constructed of another material and painted or otherwise colored black or another suitably dark color. It is also contemplated that only a transverse segment of the idler roller 225a over which a monitored, longitudinally oriented filament 103a passes need be a dark color. Moreover, instead of an idler roller 225a, the scrim 103 may be conveyed over any suitable background member, such as a flat panel (not shown) having a sufficiently dark outer surface to provide a contrasted background to the scrim filaments 103a, 103b.

The sensor 233 is desirably capable of monitoring a set width, otherwise referred to herein as a scanning range or scanning width $W_s$ (FIG. 9) of the sensor. The scanning width $W_s$ of the sensor 233 of the illustrated embodiment is desirably less than the lateral spacing $W_w$ between adjacent longitudinally oriented filaments 103a of the scrim 103 so that only one longitudinally oriented filament may be monitored by the sensor. That is, two longitudinally oriented filaments 103a cannot concurrently lie within the scanning width $W_s$ of the sensor 233. As an example, for a scrim in which the lateral spacing between longitudinally oriented filaments 103a are spaced approximately 12.5 mm, the scanning width $W_s$ of the sensor 233 is desirably about 10 mm, with the monitored longitudinally oriented filament desirably positioned generally centrally within the scanning width.

In operation of the control system 201, the scrim 103 is conveyed lengthwise from the supply roll 113 past the guide assembly 115, e.g., in contact with the idler rollers 225a, 225b and intermediate the idler roller 225a and sensor 233, to the inlet end 107 of the delivery tube 101. The sensor 233 is operated to intermittently determine the transverse position of one of the longitudinally oriented filaments 103a of the scrim, such as one of the laterally outermost longitudinally oriented filaments, within the scanning width $W_s$ of the sensor. As an example, the sensor 233 of the illustrated embodiment is operable to sense the transverse position of the filament 103a approximately 200 times per second. As an additional example, the scrim 103 may be conveyed from the supply roll 113 to the delivery tube 101 at a rate of approximately 508 cm/sec (e.g., 16 ft/sec). In such an example, the sensor 233 would therefore operate to sense the transverse position of the longitudinally oriented filament 103a approximately once for each 25.1 mm of lengthwise conveyance of the scrim 103.

Each time the sensor 233 determines the transverse position of the longitudinally oriented filament 103a within the scanning width $W_s$ of the sensor, the transverse position is communicated electronically to the guide assembly controller 227. The controller 227 compares (e.g., determines the difference between) the transverse position of the filament 103a to a target (e.g., desired or otherwise predetermined) transverse position of the filament, such as the center of the sensor scanning width $W_s$. For example, the target transverse position of the monitored longitudinally oriented filament 103a corresponds to the desired transverse alignment of the scrim 103 within the absorbent member 3 being formed within the forming chamber 41. If the determined difference exceeds a predetermined tolerance, the controller signals the drive motor of the guide assembly 115 to operably pivot the frame 223 relative to the base 221 and scrim 103 to urge transverse movement of the scrim generally toward the target transverse position of the monitored longitudinally oriented filament 103a.

While in the illustrated embodiment a single longitudinally oriented filament 103a is monitored to control the transverse position of the scrim 103, it is contemplated that two or more longitudinally oriented filaments, such as the laterally outermost longitudinally oriented filaments of the scrim, may be monitored by corresponding sensors 233 without departing from the scope of this invention. It is also understood that a longitudinally oriented filament 103a other than the laterally outermost filaments may be monitored to control the transverse position of the scrim 103. Also, the controller 227 may comprise part of the guide assembly 115, or part of the inspection device 231, or it may be constructed independent of the guide assembly and inspection device without departing from the scope of this invention.

Figure 10:
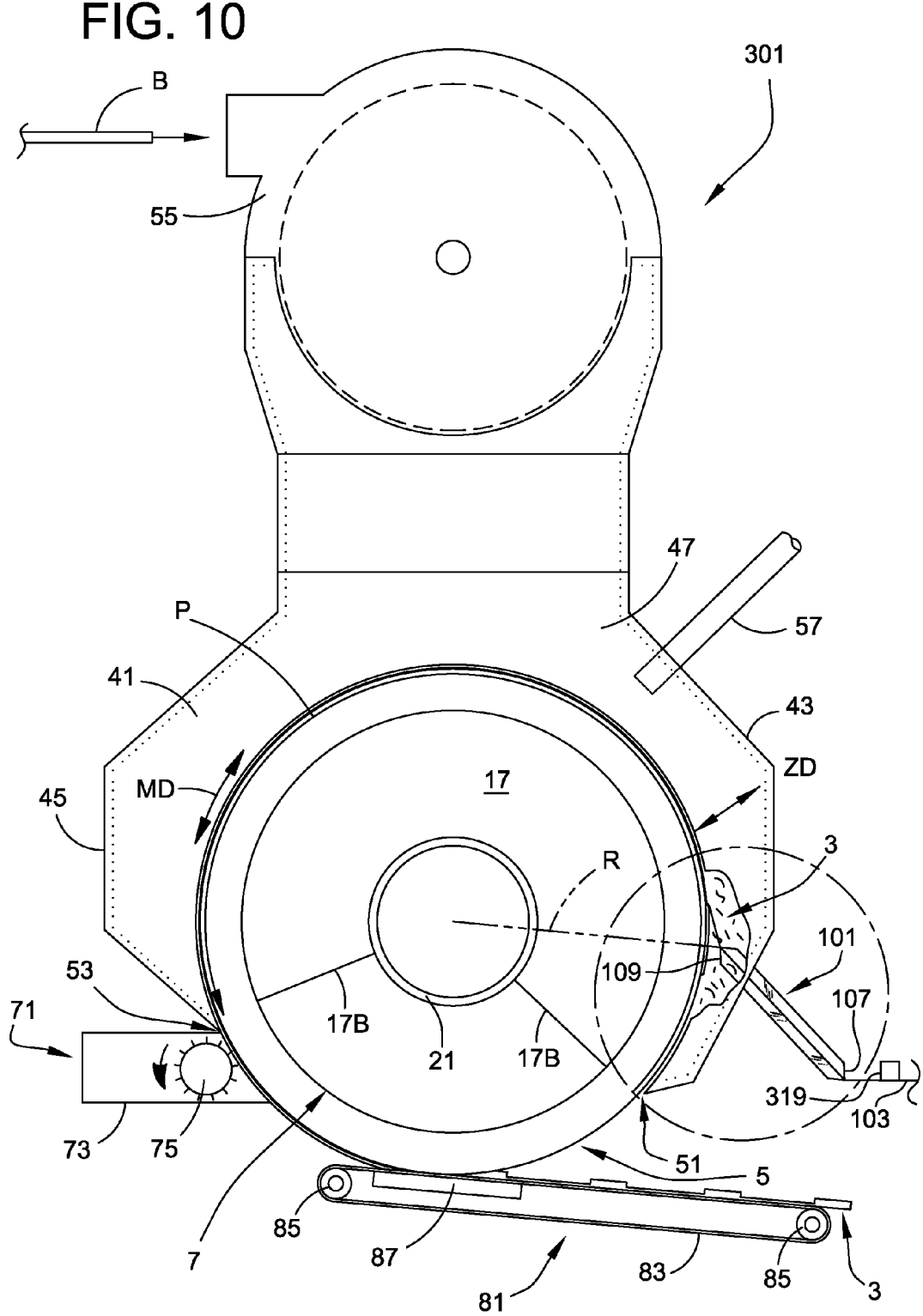
FIG. 10 is an enlarged side elevation of a portion of a second embodiment of apparatus for forming a reinforced fibrous absorbent member.

FIG. 10 illustrates a second embodiment of apparatus 301 for forming a reinforced absorbent member. The apparatus 301 is substantially the same as the apparatus 1 of the first embodiment, with the addition of a cutting device 319 (represented schematically in FIG. 10) for cutting the reinforcing web 103 into discrete longitudinally oriented filaments 103a, with laterally oriented filaments 103b or barbs extending outward therefrom, before the web overlays and is incorporated into the absorbent member within the forming chamber 41. The cutting device 319 may be any suitable cutting device such as one or more doctor blades (not shown) arranged in laterally spaced relationship with each other. The blades are positioned so that the longitudinally oriented filaments 103a pass between the blades whereby the blades cut the laterally oriented filaments 103b of the web generally centrally between the longitudinally oriented filaments. In the illustrated embodiment, the cutting device 319 is located just upstream of the delivery tube 101. However, the device 319 may be located further upstream of the delivery tube 101, within the delivery tube, at the discharge end 109 of the delivery tube, or within the forming chamber 41 intermediate the delivery tube and the forming surface 5 without departing from the scope of this invention.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. For example, features described in relation to one embodiment may be incorporated into any other embodiment of the invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for making a reinforced absorbent member including a fibrous material and a porous reinforcing web having inner and outer surfaces, said apparatus comprising:
   a forming chamber adapted to contain a fluent fibrous material;
   a forming surface moveable within the forming chamber along an arcuate path generally from an entrance of the forming chamber to an exit thereof, said forming surface being adapted to collect fibrous material thereon to form the absorbent member;
   a source of reinforcing web disposed generally exterior of the forming chamber; and
   a delivery tube having an inlet end open to the exterior of the forming chamber, a discharge end open to the interior of the forming chamber adjacent the forming surface, and a central passage extending between the inlet end and the discharge end, the delivery tube being arranged for receiving the reinforcing web from the source of reinforcing web into the central passage of the delivery tube at the inlet end thereof and guiding the web to the discharge end thereof for conveyance within the forming chamber toward the forming surface;
   said forming chamber having an opening through which the delivery tube is received into the forming chamber, said opening being disposed downstream of the forming chamber entrance generally in the direction of movement of the forming surface along said path.

2. Apparatus as set forth in claim 1 in combination with the reinforcing web wherein the delivery tube has a cross-sectional width in the range of about 0.1% to about 35% greater than the planar width of the reinforcing web.

3. Apparatus as set forth in claim 1 wherein the forming chamber is further adapted to receive superabsorbent material therein, the forming surface being further adapted to collect superabsorbent material thereon.

4. Apparatus for making a reinforced absorbent member including a fibrous material and a reinforcing web, said reinforcing web having inner and outer surfaces, said apparatus comprising:
   a forming chamber adapted to receive a fluent fibrous material therein;
   a forming surface moveable within the forming chamber and adapted to collect fibrous material thereon to form the absorbent member;
   a source of reinforcing web disposed generally exteriorly of the forming chamber; and
   a delivery tube having an inlet end open to the exterior of the forming chamber, a discharge end open to the interior of the forming chamber, and a central passage extending between the inlet end and the discharge end, at least a portion of the delivery tube adjacent the discharge end thereof extending within the interior of the forming chamber, said delivery tube being arranged for receiving the reinforcing web from the source of reinforcing web into the central passage of said tube at the inlet end thereof and guiding the web to the discharge end thereof for conveyance within the forming chamber toward the forming surface, the delivery tube being supported by the forming chamber, the inlet end and of the delivery tube being spaced outward from the forming chamber and the discharge end of the delivery tube being disposed within the forming chamber.

5. Apparatus for making a reinforced absorbent member including a fibrous material and a reinforcing web, said reinforcing web having inner and outer surfaces, said apparatus comprising:
   a forming chamber adapted to receive a fluent fibrous material therein;
   a forming surface moveable within the forming chamber and adapted to collect fibrous material thereon to form the absorbent member;
   a source of reinforcing web disposed generally exteriorly of the forming chamber; and
   a delivery tube having an inlet end spaced outward from the forming chamber and open to the exterior of the forming chamber, a discharge end open to the interior of the forming chamber adjacent the forming surface, and a central passage extending between the inlet end and the discharge end, at least a portion of the delivery tube adjacent the discharge end thereof extending within the interior of the forming chamber, said delivery tube being arranged for receiving the reinforcing web from the source of reinforcing web into the central passage of said tube at the inlet end thereof and guiding the web to the discharge end thereof for conveyance within the forming chamber toward the forming surface.

6. Apparatus for making a reinforced absorbent member including a fibrous material and a reinforcing web, said reinforcing web having inner and outer surfaces, said apparatus comprising:
   a forming chamber adapted to receive a fluent fibrous material therein;
   a forming surface moveable within the forming chamber and adapted to collect fibrous material thereon to form the absorbent member;
   a source of reinforcing web disposed generally exteriorly of the forming chamber; and
   a delivery tube having an inlet end spaced outward from the forming chamber and open to the exterior of the forming chamber, a discharge end open to the interior of the forming chamber, and a central passage extending between the inlet end and the discharge end, at least a portion of the delivery tube adjacent the discharge end thereof extending within the interior of the forming chamber, said delivery tube being arranged for receiving the reinforcing web from the source of reinforcing web into the central passage of said tube at the inlet end thereof and guiding the web to the discharge end thereof for conveyance within the forming chamber toward the forming surface, the delivery tube being disposed at an angle relative to the forming surface.

7. Apparatus for making a reinforced absorbent member including a fibrous material and a reinforcing web, said reinforcing web having inner and outer surfaces, said apparatus comprising:
   a forming chamber adapted to receive a fluent fibrous material therein;
   a forming surface moveable within the forming chamber and adapted to collect fibrous material thereon to form the absorbent member;
   a source of reinforcing web disposed generally exteriorly of the forming chamber; and
   a delivery tube having an inlet end spaced outward from the forming chamber and open to the exterior of the forming chamber, a discharge end open to the interior of the forming chamber, and a central passage extending between the inlet end and the discharge end, said delivery tube being arranged for receiving the reinforcing web from the source of reinforcing web into the central passage of said tube at the inlet end thereof and guiding the web to the discharge end thereof for conveyance within the forming chamber toward the forming surface, the delivery tube being sized and configured to permit passage of the web therethrough with the web in a generally planar configuration.

8. Apparatus for making a reinforced absorbent member including a fibrous material and a reinforcing web, said reinforcing web having inner and outer surfaces, said apparatus comprising:
   a forming chamber adapted to receive a fluent fibrous material therein;
   a forming surface moveable within the forming chamber and adapted to collect fibrous material thereon to form the absorbent member;
   a source of reinforcing web disposed generally exteriorly of the forming chamber; and
   an elongate delivery tube having an inlet end open to the exterior of the forming chamber, a discharge end open to the interior of the forming chamber adjacent the forming surface, and a central passage extending between the inlet end and the discharge end, at least a portion of the delivery tube adjacent the discharge end thereof extending within the interior of the forming chamber, said delivery tube being arranged for receiving the reinforcing web from the source of reinforcing web into the central passage of said tube at the inlet end thereof and guiding the web in a delivery direction to the discharge end thereof for conveyance within the forming chamber toward the forming surface, said delivery tube shielding the web against contact by fibrous material and having a generally aerodynamic profile in a cross section transverse to the delivery direction to minimize any disruption of fibrous material flow within the forming chamber.

* * * * *

UNITED STATES PATENT AND TRADEMARK OFFICE
CERTIFICATE OF CORRECTION

PATENT NO. : 7,568,900 B2  
APPLICATION NO. : 11/677857  
DATED : August 4, 2009  
INVENTOR(S) : Venturino et al.

Page 1 of 1

It is certified that error appears in the above-identified patent and that said Letters Patent is hereby corrected as shown below:

In Claim 4, column 19, row 9, delete "inlet end and of" and insert therefor --inlet end of--.

Signed and Sealed this

Third Day of November, 2009

David J. Kappos  
*Director of the United States Patent and Trademark Office*